United States Patent
Harris et al.

(10) Patent No.: US 8,414,600 B2
(45) Date of Patent: *Apr. 9, 2013

(54) METHODS AND DEVICES FOR REDUCING GASTRIC VOLUME

(76) Inventors: Peter S. Harris, Pacific Beach, WA (US); Barry Hal Rabin, Idaho Falls, ID (US)

(*) Notice: Subject to any disclaimer, the term of this patent is extended or adjusted under 35 U.S.C. 154(b) by 0 days.

This patent is subject to a terminal disclaimer.

(21) Appl. No.: 13/413,640

(22) Filed: Mar. 6, 2012

(65) Prior Publication Data

US 2012/0165845 A1 Jun. 28, 2012

Related U.S. Application Data

(63) Continuation of application No. 12/048,206, filed on Mar. 13, 2008, now Pat. No. 8,142,450.

(60) Provisional application No. 60/894,626, filed on Mar. 13, 2007.

(51) Int. Cl.
*A61B 17/12* (2006.01)

(52) U.S. Cl.
USPC .............. 606/139; 606/1; 606/151; 606/213

(58) Field of Classification Search .................. None
See application file for complete search history.

(56) References Cited

U.S. PATENT DOCUMENTS

| | | | |
|---|---|---|---|
| 2,808,055 A | 10/1957 | Thayer | |
| 4,165,747 A | 8/1979 | Bermant | |
| 4,724,840 A | 2/1988 | McVay et al. | |
| 5,015,250 A * | 5/1991 | Foster | 606/147 |
| 5,292,326 A | 3/1994 | Green et al. | |
| 5,332,142 A | 7/1994 | Robinson et al. | |
| 5,345,949 A | 9/1994 | Shlain | |
| 5,355,897 A | 10/1994 | Pietrafitta et al. | |
| 5,389,102 A | 2/1995 | Green et al. | |
| 5,480,406 A | 1/1996 | Nolan et al. | |
| 5,485,952 A | 1/1996 | Fontayne | |
| 5,565,004 A | 10/1996 | Christoudias | |
| 5,643,295 A | 7/1997 | Yoon | |
| 5,662,258 A | 9/1997 | Knodel et al. | |

(Continued)

OTHER PUBLICATIONS

Fusco, Pedro E.B. MD, et al., "Comparison of Anterior Gastric Wall and Greater Gastric Curvature Invaginations for Weight Loss in Rats," Obesity Surgery, vol. 17, No. 10, pp. 1340-1345 (Feb. 2007).

(Continued)

*Primary Examiner* — Corrine M McDermott
*Assistant Examiner* — T J Scherbel
(74) *Attorney, Agent, or Firm* — Speckman Law Group PLLC; Ann W. Speckman

(57) ABSTRACT

The present invention involves new interventional methods for reducing gastric volume, and thereby treating obesity. The procedures are generally performed laparoscopically and may generally be described as laparoscopic plication gastroplasty (LPG) in which, after obtaining abdominal access, spaced apart sites on a gastric wall are engaged, approximated and fastened to create one or more tissue folds forming one or more plications projecting into the gastrointestinal space. The serosal tissue may optionally be treated during the procedure to promote the formation of a strong serosa-to-serosa bond that ensures the long-term stability of the tissue plication. These procedures are preferably carried out entirely extragastrically (i.e. without penetrating through the gastrointestinal wall), thereby minimizing the risks of serious complications.

30 Claims, 24 Drawing Sheets

U.S. PATENT DOCUMENTS

| | | | |
|---|---|---|---|
| 5,700,275 | A | 12/1997 | Bell et al. |
| 5,972,021 | A | 10/1999 | Huttner et al. |
| 6,042,599 | A | 3/2000 | Huttner et al. |
| 6,086,600 | A | 7/2000 | Kortenbach |
| 6,273,903 | B1 | 8/2001 | Wilk |
| 6,478,791 | B1 * | 11/2002 | Carter et al. ............ 606/1 |
| 6,558,400 | B2 | 5/2003 | Deem et al. |
| 6,679,895 | B1 | 1/2004 | Sancoff et al. |
| 6,913,607 | B2 | 7/2005 | Ainsworth et al. |
| 6,986,451 | B1 | 1/2006 | Mastri et al. |
| 7,097,650 | B2 | 8/2006 | Weller et al. |
| 7,175,638 | B2 * | 2/2007 | Gannoe et al. ........... 606/153 |
| 7,211,094 | B2 | 5/2007 | Gannoe et |
| 7,288,101 | B2 | 10/2007 | Deem et al. |
| 7,556,647 | B2 * | 7/2009 | Drews et al. ............. 623/2.11 |
| 7,704,264 | B2 | 4/2010 | Ewers et al. |
| 7,744,613 | B2 | 6/2010 | Ewers et al. |
| 7,862,581 | B2 * | 1/2011 | Zeiner et al. ............. 606/207 |
| 8,057,490 | B2 * | 11/2011 | Harris et al. ............. 606/139 |
| 8,092,472 | B2 * | 1/2012 | Cerier ...................... 606/139 |
| 8,100,921 | B2 * | 1/2012 | Harris et al. ............. 606/139 |
| 8,142,450 | B2 * | 3/2012 | Harris et al. ............. 606/139 |
| 2002/0022851 | A1* | 2/2002 | Kalloo et al. ............. 606/151 |
| 2002/0091395 | A1 | 7/2002 | Gabbay |
| 2002/0165561 | A1 | 11/2002 | Ainsworth et al. |
| 2002/0173803 | A1 | 11/2002 | Ainsworth et al. |
| 2003/0088270 | A1 | 5/2003 | Lubbers et al. |
| 2004/0215216 | A1 | 10/2004 | Gannoe et al. |
| 2004/0225183 | A1 | 11/2004 | Michlitsch et al. |
| 2004/0225305 | A1 | 11/2004 | Ewers et al. |
| 2005/0038449 | A1 | 2/2005 | Sancoff et al. |
| 2005/0080438 | A1 | 4/2005 | Weller et al. |
| 2005/0096673 | A1 | 5/2005 | Stack et al. |
| 2005/0149072 | A1* | 7/2005 | DeVries et al. ........... 606/153 |
| 2005/0159769 | A1 | 7/2005 | Alverdy |
| 2005/0177176 | A1 | 8/2005 | Gerbi et al. |
| 2005/0216042 | A1* | 9/2005 | Gertner .................... 606/151 |
| 2005/0228415 | A1 | 10/2005 | Gertner |
| 2005/0234294 | A1 | 10/2005 | Saadat et al. |
| 2005/0234512 | A1 | 10/2005 | Nakao |
| 2005/0247320 | A1 | 11/2005 | Stack et al. |
| 2005/0250980 | A1 | 11/2005 | Swanstrom et al. |
| 2005/0251160 | A1 | 11/2005 | Saadat et al. |
| 2005/0251161 | A1 | 11/2005 | Saadat et al. |
| 2005/0251162 | A1 | 11/2005 | Rothe et al. |
| 2005/0256533 | A1 | 11/2005 | Roth et al. |
| 2005/0267529 | A1 | 12/2005 | Crockett et al. |
| 2006/0020275 | A1 | 1/2006 | Goldfarb et al. |
| 2006/0020276 | A1 | 1/2006 | Saadat et al. |
| 2006/0036267 | A1 | 2/2006 | Saadat et al. |
| 2006/0106288 | A1 | 5/2006 | Roth et al. |
| 2006/0106405 | A1 | 5/2006 | Fann et al. |
| 2006/0157067 | A1 | 7/2006 | Saadat et al. |
| 2006/0271076 | A1 | 11/2006 | Weller et al. |
| 2006/0276810 | A1 | 12/2006 | Kelleher et al. |
| 2006/0282118 | A1 | 12/2006 | Surti |
| 2006/0293701 | A1 | 12/2006 | Ainsworth et al. |
| 2007/0021760 | A1 | 1/2007 | Kelleher |
| 2007/0043384 | A1 | 2/2007 | Ortiz et al. |
| 2007/0060932 | A1 | 3/2007 | Stack et al. |
| 2007/0112338 | A1 | 5/2007 | Cohen et al. |
| 2007/0112364 | A1 | 5/2007 | Gerbi et al. |
| 2007/0173888 | A1 | 7/2007 | Gertner et al. |
| 2007/0179335 | A1 | 8/2007 | Gertner et al. |
| 2007/0276432 | A1 | 11/2007 | Stack et al. |
| 2007/0282356 | A1* | 12/2007 | Sonnenschein et al. ...... 606/153 |
| 2008/0039878 | A1* | 2/2008 | Williams et al. ............. 606/153 |
| 2008/0147112 | A1* | 6/2008 | Sheets et al. ................ 606/205 |
| 2008/0208216 | A1* | 8/2008 | Cerier ........................ 606/139 |
| 2008/0234705 | A1 | 9/2008 | Cropper et al. |
| 2008/0249561 | A1 | 10/2008 | Stokes et al. |
| 2008/0319455 | A1* | 12/2008 | Harris et al. ................ 606/139 |
| 2009/0024144 | A1 | 1/2009 | Zeiner et al. |
| 2009/0024148 | A1 | 1/2009 | Zeiner et al. |
| 2009/0024163 | A1 | 1/2009 | Zeiner et al. |
| 2009/0112232 | A1 | 4/2009 | Crainich et al. |
| 2009/0112234 | A1 | 4/2009 | Crainich et al. |
| 2009/0118762 | A1 | 5/2009 | Crainch et al. |
| 2009/0272786 | A1 | 11/2009 | Zeiner et al. |
| 2009/0275957 | A1 | 11/2009 | Harris et al. |
| 2009/0275961 | A1 | 11/2009 | Harris et al. |
| 2009/0275962 | A1 | 11/2009 | Zeiner et al. |
| 2009/0275980 | A1 | 11/2009 | Zeiner et al. |
| 2009/0276055 | A1 | 11/2009 | Harris et al. |
| 2009/0318936 | A1* | 12/2009 | Harris et al. ................ 606/139 |
| 2010/0023022 | A1 | 1/2010 | Zeiner et al. |
| 2010/0023024 | A1 | 1/2010 | Zeiner et al. |
| 2010/0023025 | A1 | 1/2010 | Zeiner et al. |
| 2010/0023026 | A1 | 1/2010 | Zeiner et al. |
| 2010/0082046 | A1 | 4/2010 | Harris et al. |
| 2010/0137887 | A1* | 6/2010 | Crockett et al. ............. 606/144 |
| 2010/0174299 | A1 | 7/2010 | Viola et al. |
| 2010/0187283 | A1 | 7/2010 | Crainich et al. |
| 2010/0187285 | A1 | 7/2010 | Harris et al. |
| 2010/0191255 | A1 | 7/2010 | Crainich et al. |
| 2010/0191258 | A1 | 7/2010 | Harris et al. |
| 2010/0191262 | A1 | 7/2010 | Harris et al. |
| 2010/0191282 | A1 | 7/2010 | Harris et al. |
| 2012/0089157 | A1* | 4/2012 | Forsell ....................... 606/139 |

OTHER PUBLICATIONS

Fusco, Pedro E.B. MD, et al., "Evaluation of Gastric Greater Curvature Invaginations for Weight Loss in Rats," Obesity Surgery, vol. 16, No. 2, pp. 172-177 (Feb. 2006).

Talebpour, Mohammad, MD et al., "Laparoscopic Total Gastric Vertical Plication in Morbid Obesity," Journal of Laparoendoscopic & Advanced Surgical Techniques, vol. 17, No. 6, pp. 793-798 (Dec. 2007).

Puccini, Carlos Elias Sales MD, "Surset Gastric Sales: An Alternative for Restrictive Bariatric Surgery," Revista Colombiana de Cirugia, vol. 23, No. 3 (Jul.-Sep. 2008).

Skrekas, George MD, "Laparoscopic Gastric Fold. Without Sleeve Gastrectomy for Obesity," http://www.skrekas.net/surg_faq.htm (Jul. 2008).

Ethicon Endo-Surgery, "Assessment of Gastric Volume reduction in Surgical Weight Loss Candidate," ClinicalTrials.gov, NCT00721227 (Jul. 9, 2008).

Zeiner, Mark S., U.S. Appl. No. 11/779,322, filed Jul. 18, 2007, USPTO Office Action Mailed Apr. 23, 2010, 13 pages.

Zeiner, Mark S., U.S. Appl. No. 11/779,322, filed Jul. 18, 2007, Applicant's Response to USPTO Office Action Mailed Apr. 23, 2010, Submitted Jul. 22, 2010, 9pages.

Talebpour, Mohammad, MD et al., "The Report of Laparoscopic Total Gastric Vertical Plication in Morbid Obesity," Surgery for Obesity and Related Diseases, vol. 2 No. 3 p. 332 (May 2006).

In re Harris, Peter S. et al, "Uspto Office Action," U.S. Appl. No. 12/392,026, filed Feb. 24, 2009 (Sep. 11, 2012).

* cited by examiner

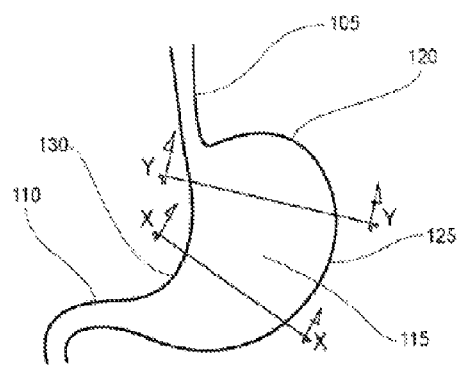
FIG. 1A
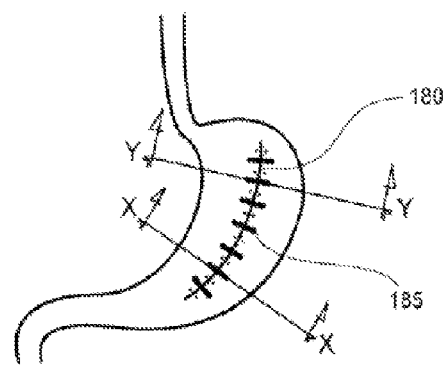
FIG. 1B
FIG. 1A1   FIG. 1A2
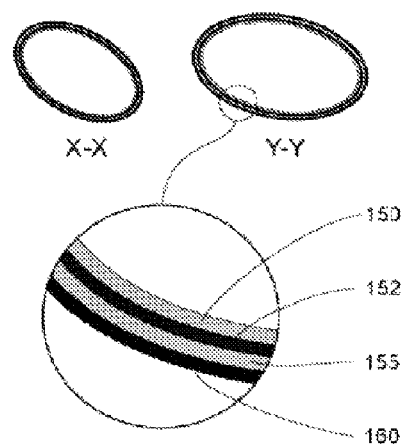
FIG. 1A3
FIG. 1B1
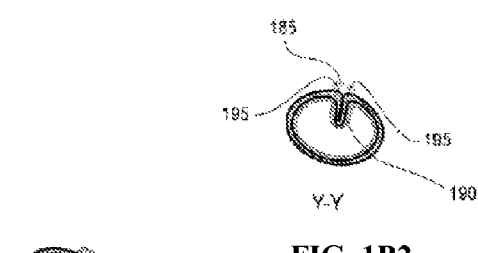
FIG. 1B2

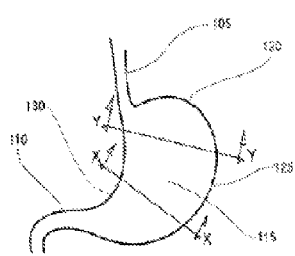
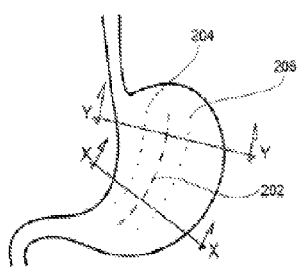
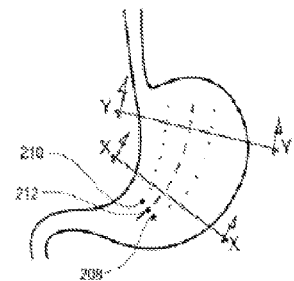
FIG. 2A  FIG. 2B  FIG. 2C
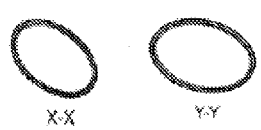
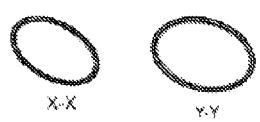
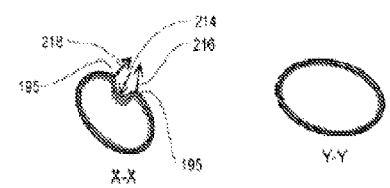
FIG. 2A1  FIG. 2A2  FIG. 2B1  FIG. 2B2  FIG. 2C1  FIG. 2C2
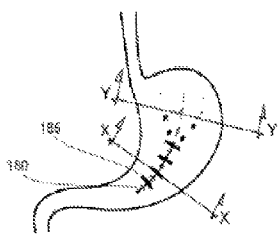
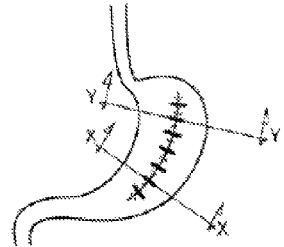
FIG. 2D  FIG. 2E
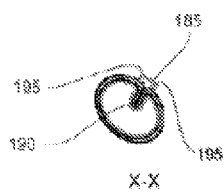
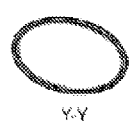
FIG. 2D1  FIG. 2D2  FIG. 2E1  FIG. 2E2

METHODS AND DEVICES FOR REDUCING GASTRIC VOLUME

CROSS-REFERENCE TO RELATED APPLICATIONS

This application is a continuation of U.S. patent application Ser. No. 12/048,206, filed Mar. 13, 2008 now U.S. Pat. No. 8,142,450, which claims priority under 35 U.S.C. §119 (e) to U.S. Provisional Patent Application No. 60/894,626 filed Mar. 13, 2007. These priority patent applications are incorporated herein by reference in their entireties.

FIELD OF THE INVENTION

The present invention relates generally to methods and devices for reducing the volume of a hollow body organ, such as gastric volume. One application of methods and devices of the present invention is treating obesity in a patient by effectively reducing the functional volume of the stomach.

BACKGROUND AND DESCRIPTION OF THE PRIOR ART

Obesity is rapidly reaching epidemic proportions in developed societies worldwide. There are currently over 1 billion overweight people globally, with 300 million of these people considered clinically obese. In the United States alone there are more than 50 million obese adults, and the numbers are expected to increase by more than 50% in the next decade. Morbid obesity (i.e. obesity in which there are secondary complications such as hypertension, diabetes, coronary artery disease, stroke, congestive heart failure, orthopedic problems and pulmonary insufficiency) not only affects quality of life, but also shortens life expectancy and costs the health care industry billions of dollars annually.

Interventional procedures and associated medical devices for treating morbid obesity in patients are well known in the art. In general, these interventional procedures promote weight loss by either (a) gastric restriction or volume reduction, (b) malabsorption, or (c) a combination of the foregoing. Gastric restriction or volume reduction methods promote weight loss by limiting the amount of food intake (i.e. the patient eats less), either due to physical space limitation or by inducing a feeling of early satiety in the patient. Malabsorption methods promote weight loss by limiting the uptake of nutrients (i.e. the patient digests less of what is eaten), usually by removing or bypassing a portion of the gastrointestinal (GI) tract.

Among the earliest interventional procedures directed at promoting weight loss were variations of the jejuno-ileal bypass developed in the 1950s. This surgery effectively bypasses the small intestine and is therefore a strictly malabsorption procedure, which poses serious risks. The bilopancreatic diversion procedure, which combines bypass of most of the small intestine with a partial gastrectomy, is a combined volume reduction and malabsorption procedure that was developed in effort to reduce these risks, but it too had complications and its success was limited.

Roux-en-Y gastric bypass surgery is a commonly performed bariatric procedure, especially in the US. It was originally performed as an open interventional procedure, but it is now routinely performed laparoscopically. This procedure utilizes interventional stapling and cutting devices to form a small stomach pouch, bypassing the lower part of the stomach, and creates a Roux-en-Y limb to attach the jejunum to the pouch. The Roux-en-Y procedure is predominantly a volume reduction method (the stomach pouch is typically ~25 cc in volume), although there is a significant malabsorption component.

Despite the proven efficacy of the Roux-en-Y procedure in terms of achieving weight loss, and the recent laparoscopic improvements that have reduced the associated interventional risks, it remains a highly invasive procedure with substantial rates of morbidity. The rate of interventional mortality may be as high as 1%, and known complications include frequent pulmonary morbidity and anastomotic leaks that can be life threatening. Furthermore, the malabsorption component of the Roux-en-Y procedure can negatively affect health because of reduced vitamin uptake, and the long-term consequences of malabsorption are not yet fully understood.

A variety of other interventional procedures have also been developed involving the use of interventional stapling to bring together and fasten opposing walls of the stomach in order to reduce its volume. Most involve malabsorption to a greater or lesser extent, depending on the procedure. Examples of such procedures include the horizontal gastroplasty (HG) and vertical banded gastroplasty (VBG), as well as more recent variations such as the Magenstrasse and Mill (M&M) and laparoscopic sleeve gastrectomy (LSG) procedures that involve not only stapling, but cutting away and removal of the unused stomach portion, leaving behind a reduced volume tube or sleeve running more or less parallel to the lesser curvature between the esophagus and the pylorus. Surgically inserted artificial sleeves that longitudinally traverse the stomach may achieve similar effective volume reductions while significantly increasing malabsorption. In any case, weight loss results achieved with these procedures may sometimes approach those of the Roux-en-Y, however these procedures are not easily performed, are difficult if not impossible to reverse, and still suffer from risks of serious complications, most frequently related to failure or leakage of the staples, which can lead to dangerous infections and even death.

An alternative minimally invasive procedure recently growing in popularity involves the laparoscopic placement of an adjustable silicone ring around the upper portion of the stomach, thereby creating a small (e.g. 50-120 cc) pouch. The LAP-BAND® is one such commercially available restrictive device that, after placement, induces a feeling of early satiety in the patient. Although considerably less invasive than the Roux-en-Y procedure, and potentially reversible, significantly less weight loss has been observed with laparoscopic banding. This procedure also suffers from a variety of limitations and shortcomings. For example, because the laparoscopic band does not actually reduce the volume of the stomach, some patients report a feeling of nearly constant hunger. Additionally, long-term complications of the laparoscopic banding procedure may include tissue erosion, slippage of the band, infection, or lack of effectiveness, frequently requiring removal of the band after a period of time.

Another less invasive alternative to the above-mentioned procedures is the intragastric balloon. The intragastric balloon is an inflatable device that is deployed within the stomach, thereby displacing a known internal volume. The advantages of this method are that it is minimally invasive, involves no malabsorption component, and requires no stapling, permanent reconfiguration or removal of tissue. While the correlation between apparent stomach volume reduction and weight loss is well established by the intragastric balloon method, the weight loss achieved is typically considerably less than with Roux-en-Y. Furthermore, unless it is surgically fastened to the stomach wall, the balloon is free floating and frequent complications such as obstruction, mucosal erosion, nausea, vomiting and pain have been documented, with the result that intragastric balloons are usually removed within 6 months after initial placement.

In effort to develop even less invasive devices and procedures, more recently there has been considerable interest in various transoral (or transesophageal) endoscopic approaches for reducing stomach volume entirely from within the gastrointestinal lumen, without the need for abdominal incisions. In general, these approaches involve advancing an endoscope down the patient's esophagus and into the stomach, whereby various tools are then used to manipulate and reconfigure the stomach tissue in order to create one or more divisions or internal folds (also known as plications) within the stomach wall. To securely hold the divisions or plications so formed, some form of sutures, staples, anchors, or other similar securing means are placed transesophageally through the stomach walls, and sophisticated endoscopic tools have been developed for such purposes. Tissue approximation and fixation devices for use in endoscopic procedures are described, for example, in U.S. Patent Publications 2004/0215216, 2007/0112364, 2005/0080438. Many other types of endoscopic tissue approximation and fixation devices and fasteners are also known in the art.

While quite promising, endoscopic approaches for reducing stomach have various limitations and shortcomings. For example, they must be performed by highly skilled endoscopic surgeons and involve the use of large, complicated endoscopic devices that require specialized training to deal with the restricted access and small working space. In order to access the stomach internally, devices must be passed down the patient's esophagus, accruing a substantial risk of perforating the esophagus and injuring adjacent organs. In addition, capturing and manipulating the tissue layers and accurately applying the securing means during a transesophageal procedure is not only difficult but also hazardous, due to the significant risk of accidental injury to other organs, bleeding, etc., when piercing (intentionally or accidentally) the stomach wall. Because there is no extragastric visualization in these procedures, there is no advance warning of a developing life threatening situation that may require a rescue operation.

The stomach wall is comprised of four main tissue layers. The mucosal layer is the innermost tissue layer, adjacent a submucosal connective tissue layer. The submucosal connective tissue layer interfaces with the muscularis layer, and the serosal layer covers the exterior (extragastric) surface. Prior art gastric reduction procedures involving tissue reconfiguration from inside the stomach require the placement of sutures, staples, or anchors during surgery to hold the reconfigured tissue in place strongly enough to sustain the tensile loads imposed by normal movement of the stomach wall during ingestion and processing of food. Because the mucosal and submucosal connective tissue layers are relatively weak and prone to elastic stretching during digestion, the securing means generally penetrate the stomach wall to engage at least the muscularis layer. For this reason, the prior art securing means are generally transgastric, passing one or more times completely through the stomach wall.

Proper use and placement of fasteners that penetrate the gastric wall is challenging and concentrates significant forces over a small surface area of mucosal tissue, thereby potentially causing the suture, staple or anchor to leak or tear through the tissue, with potentially disastrous consequences. It is well known that the fasteners used in these procedures frequently migrate, dislodge or even completely disappear over time, resulting in partial or complete failure to maintain the gastrointestinal volume reduction, as well as possible complications. These are significant limitations and shortcomings of prior art bariatric procedures involving tissue reconfiguration.

Previously known interventional procedures for treating obesity through gastrointestinal volume reduction or malabsorption thus involve numerous risks, including life-threatening post-operative complications (e.g. internal bleeding, infection), and long-term problems such as diarrhea, vitamin deficiency, electrolytic imbalance, unpredictable or insufficient weight loss, and gastrointestinal reflux disease (GERD). Given the above noted shortcomings, limitations and risks of prior art procedures, it is apparent there remains a need for safe, easy-to-perform and effective interventional procedures for reducing gastric volume, as well as for devices enabling such procedures.

SUMMARY OF THE INVENTION

The methods and devices of the present invention represent a new approach for reducing gastric volume, and thereby treating obesity and other disorders of the gastrointestinal tract, that is safe, effective, and overcomes many shortcomings and limitations of prior art procedures. In general, methods of the present invention involve reconfiguring a portion of the gastrointestinal tract (e.g., stomach wall) from the abdominal space, by contacting external tissue surfaces and drawing them toward one another to form one or more tissue invaginations, then approximating the shoulders of the extragastric tissue forming the invagination to form a tissue fold or plication, and then securing the shoulders of the extragastric tissue forming the plication to maintain a permanent plication. In preferred embodiments, the extragastric tissue is approximated such that external tissue surfaces abut one another to form the tissue plication, which extends into the internal gastric space. One or more plications may be formed to effectively reduce the circumference, and thereby cross-sectional area and volume, of the gastrointestinal lumen. One of the advantages of this procedure is that the gastric volume is reduced without reducing the mucosal surface area involved in digestive absorption. In a preferred embodiment of the present invention, the portion of the gastric tissue that is reconfigured, according to the procedure described above, is the anterior surface or anterior wall of the stomach, which is readily accessible from the intra-abdominal space. In another preferred embodiment of the present invention, which may allow for even greater gastric volume reduction, the portion of the gastric tissue that is reconfigured includes both the anterior surface and posterior surface of the stomach.

The methods of the present invention may be carried out using open interventional procedures, which are useful, for example, to penetrate the abdominal space and obtain access to difficult or remote regions of the abdomen and gastrointestinal tract, such as the stomach. Alternatively, however, abdominal access to the gastrointestinal tract (e.g., stomach) is provided using conventional laparoscopic procedures that involve relatively minimal penetration of the abdominal space. Minimally invasive non-laparoscopic methods may also be used (i.e. wherein access to the abdominal cavity is achieved without establishing a pneumoperitoneum via insufflation) to access the external surface(s) of the gastrointestinal tract. Numerous methods for accessing the internal abdominal space, and for monitoring intra-abdominal interventions (e.g., imaging and visualizing the intra-abdominal space and intervention) are known and may be used in conjunction with methods of the present invention.

According to one embodiment of the present invention, a method for reducing gastric volume comprises obtaining access to an external surface of the gastrointestinal tract (e.g. stomach); invaginating and approximating the wall of the gastrointestinal tract from its external surface to create at least one plication therein; and fastening surfaces of the approximated gastrointestinal wall to one another to secure the plication(s). According to another embodiment, a method for reducing gastric volume comprises obtaining access to an external surface of the gastrointestinal tract (e.g., stomach); invaginating and approximating the wall of the gastrointestinal tract from its external surface by drawing external surfaces of the gastrointestinal tract toward one another to form a plication extending into the interior space of the gastrointestinal tract; and fastening the approximated surfaces of the gastrointestinal wall to one another to secure the plication(s). This methodology provides a significant reduction in the internal volume of the gastrointestinal tract (e.g., stomach) without reducing the interior wall surface available for digestion and nutrient absorption.

The exterior serosal layer and adjacent muscularis layers of the gastrointestinal tract have relatively more strength than the submucosal and mucosal layers. In certain embodiments of methods of the present invention wherein external surfaces of the gastrointestinal wall are approximated to form a plication projecting into the internal space of the gastrointestinal tract, fastening of the approximated portions of the gastrointestinal wall is accomplished by penetrating fewer than all of the layers of the gastric wall. In preferred embodiments, fastening of the approximated portions of the gastric wall is accomplished by penetrating at least the thin, tough serosal layer covering the exterior of the gastrointestinal lumen and, optionally, the serosal and muscularis layers, without penetrating the submucosal and mucosal layers of the gastric wall. In these embodiments, the intragastric space is not breached during the procedure, and the mucosal layer of the gastrointestinal tract remains intact. This is advantageous not only because it simplifies the procedure, but also because it avoids a variety of known complications arising from prior art procedures that may result when transgastric methods are employed that puncture, damage or otherwise compromise the mucosa during the intervention. Thus, according to another embodiment, a method for reducing gastric volume comprises obtaining access to an external surface of the gastrointestinal tract (e.g. stomach); invaginating and approximating the wall of the gastrointestinal tract from its external surface to form a plication extending into the interior space of the gastrointestinal tract; and fastening approximated surfaces of the gastrointestinal wall to one another without penetrating all layers of the gastric wall to secure the plication(s). In one embodiment, the surfaces of the gastrointestinal wall are fastened to one another using fasteners that penetrate at least the serosal layer and preferably the serosal and muscularis layers of portions of the gastrointestinal wall forming the plication.

Additional embodiments of methods of the present invention, disclosed in detail below, incorporate additional features for the purpose of improving the safety and effectiveness and/or reducing the complexity and cost of the procedure. For example, in one embodiment of methods of the present invention, immediately prior to, or contemporaneously with the above mentioned invaginating and approximating steps, serosal tissue on surfaces of the gastrointestinal wall that adjoin to form the plication is treated to promote bonding or adhesion of adjoining tissue layers within the plication. In one embodiment, bonding of adjoining tissue layers within the plication is accomplished by disrupting the serosal tissue and promoting a healing response therein. In one preferred embodiment, a serosal tissue treatment that involves serosal tissue disruption and/or promotion of the formation of a serosal-to-serosal bond is provided over substantially the gastrointestinal surface area involved in forming the one or more tissue folds.

It is known that serosal tissue is capable forming strong adhesions to itself, or adjacent tissues, following inadvertent disruption of or damage to the serosal tissue that occurs during surgery. Typically, such adhesions are considered an undesirable and sometimes dangerous complication of abdominal surgery, and avoiding inadvertent damage to the serosa to minimize the formation of adhesions is an important goal during abdominal interventions. In contrast, in methods of the present invention, serosal tissue disruption and formation of the consequent adhesions may be optionally and intentionally promoted on targeted surface areas of the gastrointestinal lumen. When combined with the invaginating and approximating methods of the present invention, it has unexpectedly been discovered that serosal adhesions can be used beneficially for the purpose of providing a supplementary or even primary securing means for the gastrointestinal reconfiguration. According to the present invention therefore, serosal tissue on surfaces of the gastrointestinal wall that form the plication may be treated to disrupt the serosal tissue and promote a healing response for the purpose of selectively promoting the formation of a serosa-to-serosa bond across the approximated tissue boundary within the gastrointestinal plication.

A strong serosa-to-serosa bond is typically formed after a relatively brief period of time (e.g. approximately 7 days after surgery). Once formed, this serosa-to-serosa bond is sufficiently strong to substantially resist the separation forces generated by the stomach during ingestion and digestion, and ensures the long-term integrity of the plication. The formation of a strong serosa-to-serosa bond in the gastric plication of the present invention significantly improves the durability and lifespan of the plication, and consequently of the gastric reduction, and offers a significant improvement compared to the (solely) mechanical fastening methods used in tissue approximation and plication in the prior art. Thus, in the present invention, the fasteners used during the intervention to initially secure the tissue fold serve as the sole structural support for securing the plication only during the brief healing phase following surgery. Following its formation, the serosa-to-serosa bond may provide the primary structural support for securing the plication, and the fasteners initially placed to secure the plication may be removed, absorbed or, more typically, left in place within the patient to provide additional support for the plication.

In contrast to Roux-en-Y or other gastrectomy procedures involving stapling, it should be pointed out that the method of the present invention does not require cutting, transection, anastomosis, or removal of any gastrointestinal tissues from the body. It is therefore possible that the gastric reduction accomplished during this procedure is interventionally reversible. For example, if at a later date the surgeon/patient elects to reverse the gastric reduction, it is possible to substantially restore the original gastrointestinal configuration using a simple and safe procedure wherein the plication is substantially eliminated by removal of any remaining implanted securing means, followed by dissection of the serosa-to-serosa bond along the original line of tissue approximation, and subsequent localized treatment to prevent further formation of adhesions during post-operative healing.

A variety of novel devices, tools and systems are provided herein that enable a medical professional to engage and approximate soft body tissues during an interventional procedure, more safely and conveniently than possible using the prior art instruments. These inventive devices, tools and systems are useful for, among a variety of other possible interventional purposes, performing gastric reduction procedures by invaginating and approximating the wall of the gastrointestinal tract from its external surface to create at least one plication therein; and fastening surfaces of the approximated gastrointestinal wall to one another to secure the plication(s).

Gastric reduction methods of the present invention are performed in the abdominal cavity and involve contacting and manipulating the gastrointestinal tract from its external surface. The methods are typically accomplished using minimally invasive laparoscopic techniques, and the devices and systems of the present invention are therefore generally intended to be used in connection with laparoscopic techniques. However, any technique that provides access to the intra-abdominal space and, particularly, the exterior surface of the gastrointestinal tract may be used, including natural orifice transluminal endoscopic surgery (NOTES) techniques and other minimally invasive non-laparoscopic techniques.

In one embodiment, a specialized device is provided for carrying out the tissue invagination and approximation steps; another device may optionally be provided for disrupting and/or promoting the bonding of serosal tissue, and yet another device may be provided for securing the tissue plication(s). A device for invaginating and approximating gastric tissue of the present invention preferably comprises a tool having an actuation mechanism (generally on or in proximity to a handle) manipulable by an operator, at least one extendible member, and at least two tissue engagement mechanisms. Tissue engagement mechanisms are generally provided at or in proximity to the distal end(s) of the device or extendible member(s), but may be provided at other locations. In one embodiment, the approximation device comprises at least one tissue engagement mechanism provided in association with a device shaft that is inserted at the site of the intervention, and another tissue engagement mechanism provided in association with an extendible member. In this embodiment, tissue is approximated by engaging tissue at two spaced apart locations using the tissue engagement mechanisms and then moving the extendible member and the device shaft relative to one another to approximate the engaged tissue.

According to another embodiment, the approximation device of the present invention comprises at least one tissue engagement mechanism provided in association with each of at least two extendible members. The extendible members are adjustable by the operator between an insertion (collapsed, pre-deployed) condition, in which they may be inserted into the abdominal space, and an expanded (extended, deployed) condition, in which the associated tissue engagement mechanisms are separated and positioned to engage two portions of tissue spaced apart from one another. The extendible member(s) are also adjustable by the operator, by means of an actuation mechanism, following engagement of the two portions of tissue to draw together, or approximate, the two portions of tissue engaged by the tissue engagement mechanisms. The tissue engagement mechanisms are furthermore manipulable to release engaged tissue, and the extendible members are manipulable to reposition the members in a low profile, collapsed condition for withdrawal of the device from the abdominal space. Thus, in operation, the distal portion of the tissue invagination and approximation device is positioned in the abdominal space; a control feature is actuated by the operator to adjust the extendible members from a low-profile, collapsed condition to a desired extended condition; and the tissue engagement mechanisms are positioned to engage the exterior surface of spaced-apart portions of the gastrointestinal tract (e.g., stomach); a control feature is actuated by the operator to draw the tissue engagement mechanisms together and approximate the two engaged portions of tissue; the engagement mechanisms are disengaged from the tissue; and after repeating the above steps any desired number of times, the extendible members are collapsed and the device is withdrawn from the abdominal cavity.

In one embodiment, the device for invaginating and approximating gastrointestinal tissue has a selection feature that allows the medical professional to select the degree of separation of the extendible members in the expanded condition, and thereby select and control placement of the tissue engagement mechanisms and the overall size of the one or more tissue folds to provide a desired degree of gastric reduction. In another embodiment, a variety of interchangeable tools may be provided, allowing the operator to select approximation tools providing the desired placement of tissue engagement mechanisms and, consequently, the overall size of the tissue fold(s).

Another tissue invagination and approximation device of the present invention comprises a tool having at least two extendible members adjustable between a collapsed insertion condition and an extended operating condition, and additionally comprising at least one tissue invagination structure arranged and adjustable along an axis to contact and invaginate tissue located generally at a midline between the tissue portions engaged by the tissue engagement mechanisms. The tissue invagination structure is preferably axially adjustable between a withdrawn insertion condition in which it does not extend substantially beyond the terminal ends of the extendible members and an invaginating, projected condition, in which the tissue invagination structure projects toward the midline of the tissue surface engaged by the tissue engagement mechanisms. In one embodiment, the axial movement of the tissue invagination structure may be coordinated with the extension of the tissue engagement mechanisms such that, following engagement of two spaced apart portions of tissue, the tissue invagination structure is extended to contact and invaginate tissue as the approximation members are drawn together to approximate the two spaced apart tissue portions. A selection feature may allow the medical professional to select the degree of extension of the invagination structure, thereby controlling the overall size of the tissue invagination and plication, and providing a desired degree of gastric reduction.

In yet another embodiment, a serosal treatment device may be provided and used separately from or in coordination with the tissue approximation and invagination device. A serosal tissue treatment device, in one embodiment, is adapted to disrupt serosal tissue lying between spaced apart tissue surfaces engaged by the approximating members to promote healing and formation of a serosal-to-serosal bond between serosal tissue surfaces contacting one another in the plication formed during the tissue approximation. The serosal treatment device may utilize one or more mechanical structures, such as a discontinuous or a non-smooth surface structure, to disrupt serosal tissue and thereby promote serosal tissue adhesion. Additionally or alternatively, the serosal treatment device may be operated to facilitate application or administration of an agent that promotes serosal tissue disruption and/or healing in serosal-to-serosal bonds, or to administer a tissue bonding agent that promotes serosal-to-serosal tissue bonds. The serosal treatment device may incorporate an alternative modality for serosal tissue treatment, e.g., by application of heat, RF radiation, ultrasound, electromagnetic radiation, or other types of radiating energy. In one embodiment, the serosal tissue treatment device may be integrated with the approximating members and/or the tissue invagination structure, as described more fully below.

A separate tissue securing or fastening device may be provided for fastening the two adjacent portions of approximated tissue to one another to secure the plication. Suitable devices, such as suturing, stapling and other types of mechanical tissue fastening devices are well known in the art. The tissue fastening device, in one embodiment, is a multi-fire device that is capable of administering multiple fasteners, in multiple positions along a line of approximated tissue, without requiring removal from the abdominal space. Various types of fasteners and fastening devices may be used, as described more fully below.

In another embodiment, an integrated device may be provided for carrying out the tissue invagination and approximation steps, and for optionally treating serosal tissue in the invaginated tissue, while a separate device may be provided for securing the tissue plication. This beneficially eliminates the need for at least one laparoscopic incision and trocar during the procedure. In yet another embodiment, a single multi-functional device is provided that comprises tools capable of invaginating and approximating tissue, optionally treating the serosal tissue to promote a healing response, and for securing the tissue fold to produce the plication. In this embodiment, a single minimally invasive laparoscopic device is provided, thereby minimizing the number of trocars needed to complete the procedure. For example, assuming one access port is needed for the video camera and one is needed for a grasper, liver/organ manipulator, dissector, or other tissue manipulation device, the procedure may be completed using only 3 trocars. In another embodiment, the single integrated minimally invasive laparoscopic device may be optionally configured having one or more extra service channels through which the camera and other tissue manipulation devices may be inserted, thereby allowing the entire gastric reduction intervention to be completed using only a single access port. In comparison, 5 or more laparoscopic incisions are commonly needed for the Roux-en-Y procedure. Using a multi-functional tool of the present invention, the gastric reduction procedure is less invasive, requires less time to complete and therefore reduces the risks attendant any intervention, speeds patient recovery, and reduces the overall cost of treatment.

Other embodiments of medical devices of the present invention further incorporate novel tool configurations, detailed below, that enable and simplify the steps of securing the one or more tissue folds created in order to produce the one or more plications in the wall of the gastrointestinal tract. In one embodiment, means are provided for delivering individual tissue anchors comprising a securing assembly. In yet another embodiment, individual tissue anchors are reconfigured from a first state (e.g. a configuration used for delivery) to a second state (e.g. a deployed configuration). In yet another embodiment, the deployed securing assembly is configured to penetrate only the serosal and muscularis tissue layers, without penetrating completely through the wall of the gastrointestinal tract.

According to the brief summary provided above, it is apparent that methods and devices of the present invention offer several advantages over the prior art. For example, because the one or more gastric tissue plications produced may achieve substantial therapeutic gastric reductions, it is possible to obtain weight loss results comparable to prior art procedures using an interventional alternative that may be performed using minimally invasive laparoscopic or non-laparoscopic abdominal access procedures, while at the same time avoiding a variety of complications associated with malabsorption, the long-term presence of restrictive devices within the body, leakage or failure at transgastric anastomosis or anchoring sites, permanent restructuring of the gastrointestinal tract, and the like. Gastric reduction procedures of the present invention are therefore simpler, easier to perform, and safer that prior art interventional methods. In addition, the methods of the present invention, which may optionally be performed substantially or entirely extragastrically, may be carried out by conventionally skilled laparoscopic surgeons, requiring minimal specialized training to achieve substantial gastric volume reduction and effective weight loss results, while significantly reducing the risk of injury or damage to neighboring organs and other complications. This is a significant advantage compared to prior art transesophageal endoluminal interventional methods.

While the present invention will be described more fully hereinafter with reference to the accompanying drawings, in which particular embodiments are shown and explained, it is to be understood that persons skilled in the art may modify the embodiments herein described while achieving the same methods, functions and results. Accordingly, the descriptions that follow are to be understood as illustrative and exemplary of specific structures, aspects and features within the broad scope of the present invention and not as limiting of such broad scope.

BRIEF DESCRIPTION OF THE FIGURES

FIG. 1 schematically illustrates an interventional method according to one embodiment of the present invention, pre-procedure (FIGS. 1A-1A3), and post procedure (FIGS. 1B-1B2).

FIGS. 2A-2E2 schematically illustrate an exemplary interventional gastric reduction method according to one embodiment of the present invention.

FIGS. 5A-5F illustrate operation of a medical device according to one embodiment of the present invention, wherein FIG. 5A shows an overview; FIG. 5B shows a close-up, distal end of the device in a collapsed state; FIG. 5C shows a close-up, distal end of the device in an extended state; FIG. 5D shows the device in an extended state following tissue engagement; FIG. 5E illustrates partial retraction of the extendible members and tissue engagement mechanisms and actuation of a projecting serosal tissue treatment member during invagination and approximation; and FIG. 5F illustrates complete retraction of the extendible members and full extension of the projecting serosal tissue treatment member to form the plication.

FIGS. 6A-6D illustrate a medical device system according to one embodiment of the present invention, wherein FIG. 6A shows separate tools positioning; FIG. 6B shows the tissue fold created; FIG. 6C shows the fasteners applied; and FIG. 6D shows a plurality of fasteners.

FIGS. 7A-7H illustrate a medical device according to one embodiment of the present invention, wherein FIG. 7A shows an overview; FIG. 7B shows the distal end in collapsed state; FIG. 7C shows the distal end in expanded state; FIG. 7D shows the tissue engagement; FIG. 7E shows the tissue invagination and approximation; FIG. 7F shows the tissue fold created; FIG. 7G shows the securing means applied, with the distal end retracted to collapsed state; and FIG. 7H shows a plurality of securing means.

FIGS. 8A-8E illustrate a medical device according to another embodiment of the present invention, wherein FIG. 8A shows the distal end of a tissue approximation device in a collapsed state and FIG. 8B shows a helical fastener for use in the tissue approximation device of FIG. 8A; FIG. 8C shows a tissue fold created; FIG. 8D shows the fasteners applied and the distal end retracted to collapsed state; and FIG. 8E shows a plurality of fasteners applied.

FIGS. 9A and 9B illustrate an embodiment of the present invention, wherein FIG. 9A shows a first tissue fold created and first fastener applied to produce first plication; and FIG. 9B shows a second tissue fold created and a second fastener applied producing second plication.

DETAILED DESCRIPTION OF THE INVENTION

Figure 3A:
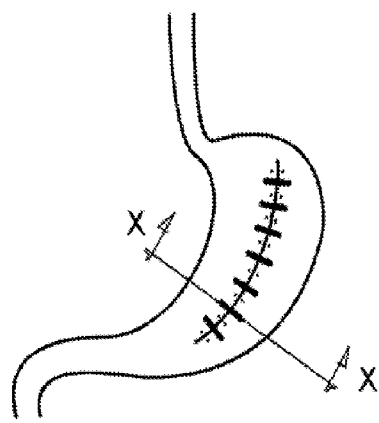
FIGS. 3A and 3B show an organ having a plication and a cross sectional view of a plication, illustrating securing means applied according to one embodiment of the present invention.

Methods of the present invention provide effective reduction of the functional volume of the gastrointestinal tract (e.g., stomach) using an extragastric gastroplasty procedure. In this procedure, a portion of the gastrointestinal tract is reconfigured by invaginating and approximating tissue to form one or more tissue folds, and then securing the one or more tissue folds in order to produce one or more plications. While the following detailed descriptions refer in general to reducing the functional volume of the gastrointestinal tract, the stomach in particular, it should be recognized that the invagination, approximation and securing methods of the present invention may be used on other body tissues and for other interventional purposes, within the scope of the present invention.

Gastric reduction procedures of the present invention generally access the gastrointestinal tract via the abdominal cavity. This is most typically accomplished using conventional laparoscopic techniques wherein the patient is anesthetized, one or more small incisions are made through the abdominal wall, and a pneumoperitoneum is established by insufflation, thereby allowing the insertion of imaging devices and one or more interventional instruments through laparoscopic ports, also known as trocars. Alternatively, methods of the present invention may also be carried out when access to the abdominal cavity and gastrointestinal tract is obtained using even less invasive, non-laparoscopic techniques. A variety of such non-laparoscopic techniques may be utilized within the scope of the present invention, typically involving grasping and lifting, or otherwise retracting the abdominal wall to create sufficient working space within the abdominal cavity, without the need for insufflation. Alternatively, the methods and devices of the present invention may also be adapted for flexible endoscopic use, allowing access to the abdominal cavity and external surface of the gastrointestinal tract to be obtained by first entering the body through a natural orifice (e.g esophagus, anus or vagina), then penetrating through the wall of an anatomical lumen into the abdominal cavity.

Once abdominal access has been obtained, the medical professional employs one or more cameras or other imaging devices, along with a variety of tools known in the art, to manipulate the internal organs and/or tissues to expose the region of the gastrointestinal tract of interest. In preferred embodiments of the present invention, at least the anterior portion of the stomach is exposed sufficiently to allow for its reconfiguration. This may require dissection and/or removal of at least a portion of the omentum, and it may require lifting and/or partial retraction of the liver, both of which are relatively simple interventional steps that are well known in the art. The subsequent reconfiguration and gastric reduction may then be performed, preferably using the devices and systems of the present invention, which are described in detail below.

FIG. 1 schematically illustrates the relevant portion of the gastrointestinal tract (anterior view), both pre-procedure (FIG. 1A) and post-procedure (FIG. 1B). To aid in the following discussion, it is helpful to first distinguish the various anatomical structures in FIG. 1A. The stomach itself lies between the esophagus 105 and pylorus 110. The anterior wall 115 of the stomach is shown, along with the fundus 120, the greater curvature 125, and lesser curvature 130. Two cross-sectional views of the stomach are shown in FIG. 1A1 at X-X and in FIG. 1A2 at Y-Y. It is helpful to point out the major tissue layers of the stomach wall, as illustrated in FIG. 1A3. Starting intragastrically and moving outward, the innermost tissue layer is the mucosal tissue layer 150, then there is a submucosal connective tissue layer 152, the muscularis tissue layer 155, and the exterior serosal tissue layer 160 that covers the extragastric surface of the stomach.

FIG. 1B illustrates a stomach following gastric reduction according to methods of the present invention. As shown in FIGS. 1B1 and 1B2, the stomach now exhibits a significantly reduced cross sectional area (e.g. at X-X and Y-Y) and the functional volume of the stomach has been decreased approximately 50% as a result of single fold 180 being placed in the anterior wall 115 of the stomach. As shown, fold 180 is located approximately midway between the greater curvature 125 and lesser curvature 130, and extends approximately longitudinally from near fundus 120 to near pylorus 110. As can be seen in sections X-X and Y-Y of FIGS. 1B1 and 1B2, fold 180 was created by invaginating and approximating the tissue of the anterior wall 115 of the stomach so as to bring the serosal tissue layer 160 into contact with itself. Fasteners are then applied to the tissue brought together to produce the plication in the wall of the stomach.

In a preferred embodiment of the present invention, a single fold and plication is produced in the above described manner and location, as illustrated in FIG. 1B; however, in other embodiments, two or more such plications may be produced. Although the plication is illustrated as being formed approximately midway between the greater and lesser curvatures of the stomach, it will be appreciated that other areas of the stomach or gastrointestinal wall may be used, as may be necessary based on individual anatomy and the surgeon's desire to achieve the targeted functional gastric reduction, while minimizing the overall invasiveness of the procedure. According to the present invention the functional volume of the stomach is preferably decreased at least 20%, is more preferably decreased at least 30%, and is most preferably decreased at least 40%. In morbidly obese patients, a functional volume reduction of 50% or more may be achieved in order the promote the desired excessive weight loss.

In FIG. 1B, securing means comprising a row of individual staples 185 are placed substantially along the length of fold 180. As shown in FIG. 1B2 at section Y-Y, staples 185 grasp tissue shoulders 195 that are formed where the opposing tissue layers of the tissue fold intersect the circumference of the stomach. As can also be seen in section Y-Y, according to a preferred embodiment of the present invention, staples 185 engage tissue shoulders 195 by penetrating only through serosal tissue layer 160 and underlying muscularis tissue layer 155, without penetrating completely through the stomach wall to breach or otherwise compromise mucosal tissue layer 150. As can also be seen in section Y-Y, according to another preferred embodiment of the present invention, the approximated tissue surfaces within the tissue fold are configured such that there is substantially intimate serosal-to-serosa contact within the plication 190.

FIG. 2 illustrates in greater detail the intermediate steps of the procedure, according to one embodiment of the present invention. FIG. 2A and FIG. 2E are identical to FIG. 1A and FIG. 1B, respectively, and are repeated for completeness. FIG. 2B, FIG. 2C and FIG. 2D are helpful to explain other aspects of the intermediate steps. In FIG. 2B, for example, prior to commencing with the reconfiguration portion of the procedure, the region of interest on anterior wall 115 may be visually identified, marked or mapped out to aid subsequent steps of the procedure. For example, it may be desirable to identify and/or indicate the target position and length of the fold centerline 202, as well as the bounding lines 204 and 206 where the tissue will be contacted, engaged and/or secured. The location of bounding lines 204 and 206 define the depth of the tissue fold to be created, as well as the surface area of tissue that will be approximated during creation of the tissue fold. Identification, marking and/or mapping of the tissue structures and/or locations can be carried out according to methods well known in the art, for example, inks, dyes, adhesives, implantable tags, clips, fasteners, radio-opaque markers, fluorescent markers, cauterizing marks, and the like, may be used.

FIG. 2C schematically illustrates the early steps in the procedure, starting at one end of the target area (e.g. near the pylorus) and working progressively in one direction (e.g. toward the fundus). It should be recognized, however, that this progression is optional, and that it is just as feasible to start near the fundus and work toward the pylorus, to start anywhere along the length of the intended fold and work in both directions, or any combination of the foregoing. To form a tissue fold, the tissue is contacted and/or engaged at two or more locations, and various combinations of relative motions are then used to ensure the tissue is invaginated as the opposing tissue surfaces are approximated. Examples of such combinations of relative motions include one or more motions selected from the group consisting of pushing motions, pulling motions, twisting motions, and shearing motions.

In FIG. 2C, for example, tissue is contacted and engaged at locations 208 and 210 on opposite sides of a fold centerline location 212. Relative motion between central location 212 and the tissue contact and engagement locations 208 and 210, is represented in FIG. 2C1 by pushing force vector 214 and pulling force vectors 216 and 218, respectively. These motions invaginate the tissue and approximate the opposing tissue surfaces, while bringing tissue shoulders 195 toward each other for subsequent securing. The relative motion illustrated may be achieved, for example, by holding central location 212 substantially stationary and pulling the tissue engagement points 208 and 210, or by holding the tissue engagement points 208 and 210 substantially stationary and pushing on the central location 212, or alternatively, any combination of pushing and pulling may be used to achieve the same effect.

After the tissue has been approximated to create the tissue fold 180 as described above, and tissue shoulders 195 have been brought together into proximity of one another, a tissue fastener 185 is then applied at that location to secure the plication 190, as shown in FIG. 2D. In FIG. 2D, exemplary tissue fastener 185 is schematically shown as a box-type of interventional staple, similar in form and function to a box-type staple known in the art of interventional skin stapling for use in wound closure applications. However, it should be obvious to those skilled in the art that, within the scope of the present invention, a wide variety of mechanical elements may be used as tissue fasteners 185 for the purpose of anchoring, fastening, holding, attaching, or otherwise securing tissue surfaces 180 to produce plication 190. Examples of suitable tissue fasteners that may be used include but are not limited to sutures, staples, screws, tacks (e.g. U-shaped, circular and helical fasteners), clips, hooks, clamps, t-tags, and the like. In a preferred embodiment of the present invention, tissue fasteners 185 are preferably applied at least directly across tissue shoulders 195 at more than one location along the length of tissue fold 180, more preferably at several relatively closely spaced locations to secure the plication.

The tissue engagement, approximation and fastening steps are repeated any number of times as is necessary to completely form and secure the one or more tissue plications. In the example provided herein, the final result is shown schematically in FIG. 2E.

For convenience, the procedure may progress sequentially in one direction along the length of the intended fold, as illustrated in FIG. 2D, effectively producing the plication in a manner similar to closing a zipper. However, sequential advancement is not required, and the surgeon may use discretion in deciding where to begin and how to advance the procedure. At each of one or more locations along the length of the intended fold, the tissue is invaginated, approximated and secured with one or more tissue fasteners before moving to the next location. In one embodiment, a device may be provided that allows simultaneous or sequential placement of multiple tissue fasteners while the invaginating and approximating tool is placed and held at one location. Alternatively, in another embodiment, a device may be provided that allows placement of a single tissue fastener along a substantial length, or even along the complete length, of the tissue fold, while the invaginating and approximating tool is held at one location.

According to one embodiment of the present invention, prior to securing the approximated tissue to produce the one or more plications, at least a portion of the surface area of the serosal tissue enfolded by the one or more plications is selectively treated to promote serosal-to-serosal tissue bonding. There is a considerable body of clinical knowledge regarding the mechanisms of abdominal adhesion formation, and a variety of methods known to those skilled in the art may be used to selectively treat the serosal tissue surfaces to promote tissue adhesion of the serosal tissue layers adjoining one another inside the tissue fold forming the plication. Examples of such tissue treatments include but are not limited to mechanical disruption methods (e.g. abrasion), energy deposition methods (e.g. RF, ultrasonic, electromagnetic, and the like), methods involving treatment using liquids (e.g. chemicals, pharmaceuticals, adhesives, etc.) and methods involving treatment using solids (e.g. powders, films, etc.). Regardless of the tissue treatment method used, an important aspect of this embodiment is that serosal tissue bonding or adhesion is promoted over a sufficiently large interfacial surface area across the approximated tissue boundary within the plication to achieve a strong and durable serosa-to-serosa bond postoperatively.

Figure 3B:
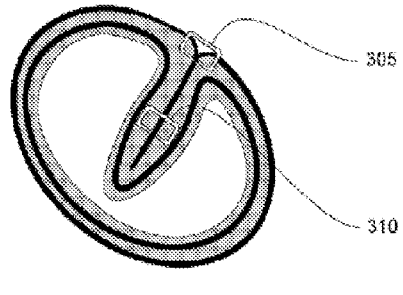

In yet another embodiment of the present invention, additional tissue fasteners may also be optionally applied while the tissues are being approximated to aid in forming, stabilizing and/or providing additional strength to the resulting tissue plication, as well as to further promote the formation of a strong serosa-to-serosa bond inside the plication. For example, as illustrated in the enlarged cross sectional view X-X shown in FIG. 3B, in addition to outer tissue fastener 305 (similar to the tissue fastener 185 described previously), one or more additional internal tissue fastener 310 may be applied across the contact area of the approximated tissue surfaces within the fold while it is being formed, such that after the plication is completed, the one or more additional internal tissue fasteners 310 are located inside the plication for the purpose of better securing the tissue across the approximated tissue surfaces. Additional internal tissue fastener 310 may be identical to outer tissue fastener 305, being placed by the same device, or in an alternative embodiment, additional internal tissue fastener 310 may have a different design and/or be placed using additional devices. Note that additional internal tissue fastener 310 also preferably penetrates only the serosal and muscularis tissue layers. Although FIG. 3 illustrates the use of a box-type staple, as in the case of tissue fastener 185 described previously, this embodiment is merely illustrative and a wide variety of alternative fasteners exist that may be used for the outer tissue fastener 305 and additional internal tissue fastener 310, within the scope of the present invention.

Figure 4A:
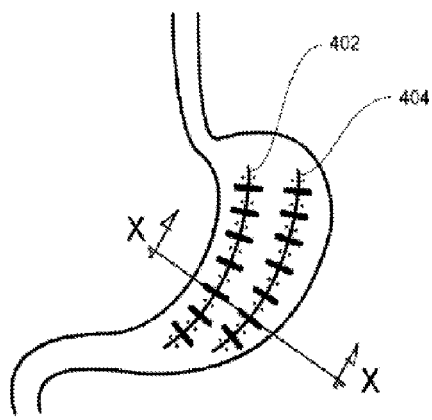
FIGS. 4A and 4B show an organ having two plications and a cross sectional view of the multiple plications according to one embodiment of the present invention.
Figure 4B:
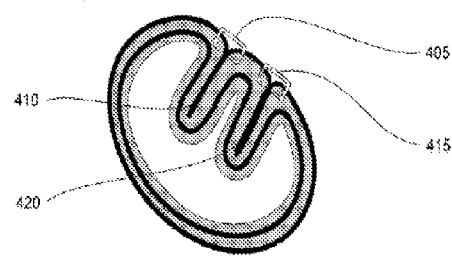

In yet another embodiment of the present invention, more than one tissue plication may be produced according to the previously described methods. For a variety of reasons, it may be advantageous in some cases to produce two or more plications. These advantages may include, for example, allowing a greater range of effective volume reductions in the stomach to be achieved, allowing smaller laparoscopic devices to be used, allowing the surgeon more flexibility in positioning of the plications relative to the stomach or surrounding organs, for reducing the maximum forces generated on the individual securing means, and so on. FIGS. 4A and 4B schematically show an example according to one embodiment of the present invention in which tissue two adjacent tissue folds 402 and 404 have been placed in the anterior wall of the stomach, running more or less parallel to one another. As can be seen in FIG. 4B in the enlarged view of cross section X-X, tissue fold 402 has been secured with tissue fastener 405 to produce a first plication 410, whereas tissue fold 404 has been secured with tissue fastener 415 to produce a second plication 420. It should be obvious to those skilled in the art that within the scope of the present invention, it is possible to produce any number of individual and separate plications in the manner described previously, each of which plication may be characterized individually in terms of length, depth, position, number and type of fasteners placed, and so on, to achieve the intended interventional result.

Interventional Devices and Systems

Interventional devices for performing methods of the present invention are described herein that, taken together, comprise systems of the present invention. The devices and systems of the present invention provide the ability to carry out the above described volume reduction procedures in a safe, efficient and minimally invasive manner, which is difficult or impossible to accomplish using prior art devices. It will be appreciated that while the devices and systems of the present invention are described below with respect to their use in gastric reduction methods of the present invention, they have utility and may be used for general approximation and fastening of other types of soft body tissues and in other types of interventional procedures as well.

In general, at least one handheld interventional instrument is provided having one or more integrated tool assembly(ies) adapted for placement at an interventional site, such as within the abdominal cavity, in combination with one or more actuator(s) positioned remotely from the tool assembly and providing operator control of the tool assembly(ies) during an intervention. The tool assembly is preferably capable of engaging tissue at two or more separate locations, and then invaginating and approximating tissue to effectively create a tissue fold between the tissue engagement locations. In one embodiment, the tool assembly comprises at least two tissue engagement mechanisms (e.g. clamps, grippers, forceps, jaws, hooks, barbs, vacuum ports or the like, or combinations of these mechanisms) positioned at or in proximity to the distal end of an elongate shaft of a laparoscopic device. The tissue engagement mechanisms may be positionable by means of a remote actuator, or they may be mounted on supporting members that may be positionable to engage desired tissue sites. Using this device, the laparoscopic shaft is positioned within the abdominal cavity, and the distal end of the shaft is positioned at a first desired tissue engagement site, where a tissue engagement mechanism is engaged with the tissue. The operator then repositions the shaft by moving it to a second location, dragging the first engaged tissue location toward the second, and thereby approximating the first and second tissue locations. The approximated tissues may then be fastened to one another to secure the plication using fasteners applied with an independent device or an integrated assembly of the tissue approximation device.

In another embodiment, a first tissue engagement mechanism may be positioned at the distal end of the elongate shaft of a laparoscopic device, while a second tissue engagement mechanism may be positioned at the distal end of an extendible member that can be manipulated by an operator to move away from the axis of the device shaft to position the second tissue engagement mechanism at a second location, remote from the distal end of the device. The extendible member may be substantially rigid, or it may be flexible, or it may have both substantially rigid and flexible portions, and it may either be deployable from inside the elongate shaft of the laparoscopic device, or attached near the distal end of the shaft by mechanical means. In one embodiment, a proximal end of an extendible member is attached near the distal end of the elongate shaft using a pivot connection, a hinge connection, a flexible connection, or the like, that allows the extendible member to be operatively and selectively actuated to move its distal, operating end (comprising a tissue engagement member) away from the axis of the laparoscopic device to engage tissue. In operation, the distal end of the shaft of the laparoscopic device is first positioned at a desired tissue surface and the tissue is engaged at a first site. The extendible member and its associated tissue engagement mechanism is then deployed, extending away from the axis of the shaft to independently engage tissue at a second location. The extendible arm and its associated tissue engagement mechanism is then retracted, under control of the operator, and the second engaged tissue location is drawn in toward the axis of the shaft and thereby approximated adjacent the first engaged tissue site. An invaginated tissue fold projecting away from the distal end of the device and into the gastrointestinal space is created as the two tissue sites are drawn together and approximated.

In other embodiments, described in detail below, two or more such extendible members are provided on an interventional device, each extendible member having at least one tissue engagement mechanism, generally (but not necessarily) positioned at its distal end, such that the engagement of tissue at multiple separate locations can be accomplished without requiring the shaft of the laparoscopic device itself to contact the tissue surface. The extendible members may be actuated and positioned separately and independently of one another, or they may be actuated and positioned simultaneously and in coordination with one another. Operation of this type of device involves deploying each of the extendible members and their associated tissue engagement mechanisms, independently or in coordination, to contact the tissue engagement mechanisms at two locations on the tissue, then approximating the engaged tissue to form an invaginated tissue fold by moving at least one of the extendible members toward the other and, in some embodiments, by moving multiple extendible members toward a central location, thereby approximating the engaged tissue substantially near the distal end of the device (or along a longitudinal axis extending therefrom).

Another embodiment that provides an alternative to using two or more extendible members to engage tissue involves the use of tethers. In this case, the distal end of the shaft of a laparoscopic instrument may be positioned to sequentially engage tissue at each of two or more locations using releasable tissue engagement mechanisms mounted on retrievable tethers, wherein each tissue engagement mechanism, after being engaged in tissue, is released from the end of the shaft of the laparoscopic instrument, yet remains connected to the instrument by a tether (e.g. a suture, wire, or the like). This allows the instrument to be moved freely between each desired tissue engagement location to deploy two or more tissue engagement mechanisms at different tissue sites. Subsequently, the tethers may be selectively retrieved, or retracted back toward the shaft of the device to draw the engaged tissue sites toward one another, thereby approximating the tissue sites. Alternatively a cinching member through which the flexible tethers pass may be slid distally down the length of tethers, causing the engaged tissue locations to move toward each other, thereby approximating tissue. Retrieval of the tether(s) and/or operation of the cinching member(s) is under the control of an operator using associated actuation mechanisms.

It will be appreciated that methods and systems of the present invention may be used in connection with other diagnostic and therapeutic methods and devices. Methods of the present invention may thus be used, for example, in connection with conventional diagnostic and therapeutic methods and may involve the administration of diagnostic or therapeutic agents, agents for visualizing the interventional site, and the like. Similarly, device components of the present invention may be used in connection with various procedures and agents that are known in the art. Certain device components that are intended for introduction to the interventional site, such as tissue engagement mechanisms, probes, extendible members, fasteners, and the like may be administered in association with various types of diagnostic or therapeutic agents, or may be coated or impregnated with such materials. Suitable agents may include clotting agents, healing agents, hydrophobic and/or hydrophilic materials, agents promoting lubricity, and the like.

Figure 5A:
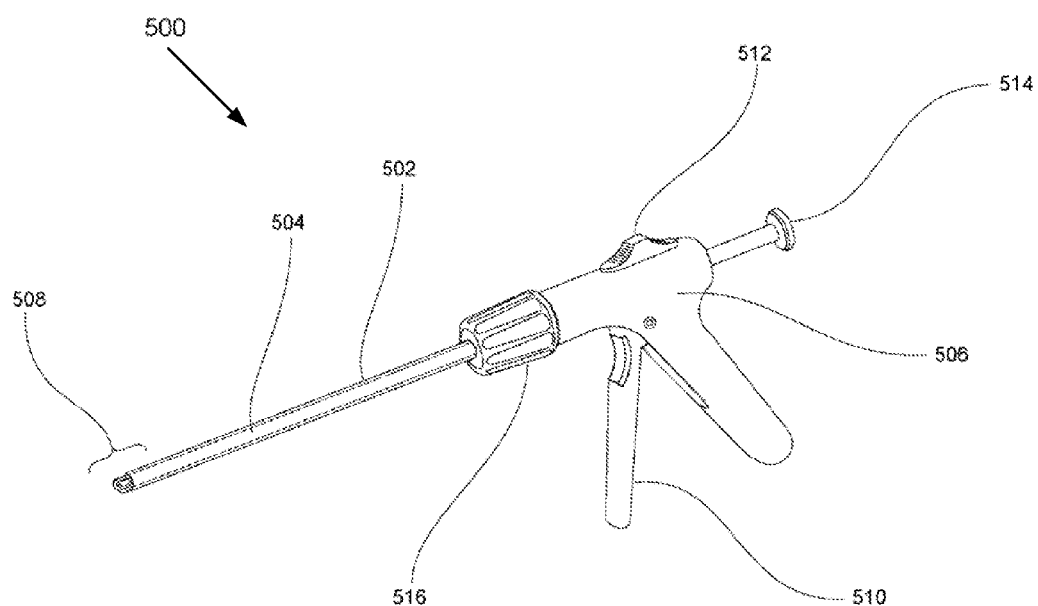
Figure 5B:
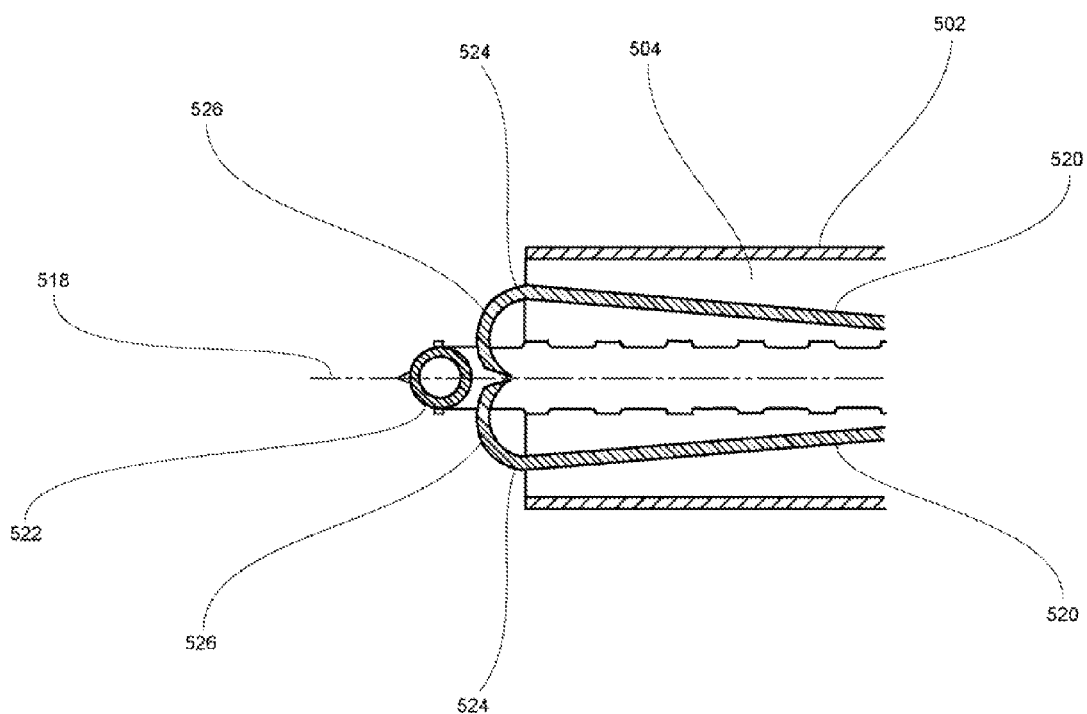

FIGS. 5A-5F illustrate an exemplary tissue approximation device according to one embodiment of the present invention. An overview of device 500 is shown in FIG. 5A in the pre-deployed configuration, and FIG. 5B shows a distal end of device 500 in the deployed configuration. Device 500 comprises an elongate tubular member 502 having at least one internal working channel 504, handle assembly 506 positioned at the proximal end, and approximating tool assembly 508 positioned at the distal end, wherein approximating tool assembly 508 is shown in the collapsed (i.e. pre-deployment or fully retracted) state, substantially confined within working channel 504. In the case of minimally invasive laparoscopic surgery, this low profile collapsed state configuration is useful for delivery of the instrument to and removal of the instrument from an internal site in the patient, such as the abdominal cavity, through a standard trocar. It is therefore generally desirable that the outer diameter of elongate tubular member 502 be as small as possible, preferably 15 mm or less, more preferably 12 mm or less and, in some embodiments, 5 mm or less. Also shown in FIG. 5A, actuating mechanisms such as a trigger 510, slider 512, and plunger 514 are provided in connection with handle assembly 506. Also shown is rotating collar 516 that allows the orientation of handle assembly 506 to be independently adjusted by the operator relative to the orientation of approximating tool assembly 508.

FIG. 5B shows an enlarged cross section view of the distal end of device 500, with approximating tool assembly 508 being shown in the collapsed state. In this configuration, located along longitudinal axis 518 of working channel 504 are two (or more) extendible members 520, and pushing member 522, each being operatively connected to an actuating mechanism operated at the handle assembly 506, as described below. Each of said extendible members 520 is configured at its distal end with a tissue engagement mechanism 524 comprising one or more mechanisms for controllably and selectively grasping, grabbing, gripping, piercing, holding or otherwise engaging tissue. In the example shown, tissue engagement mechanism 524 incorporates a tissue hook 526. Hook 526 has a generally pointed distal end for penetration of tissue and has a relatively short curved segment, thus limiting the degree of tissue penetration. Tissue engagement mechanisms having a generally pointed and sharp tissue penetration structure for penetrating tissue, such as the relatively tough serosal layer forming the exterior gastric wall, are preferred in many embodiments.

Figure 5C:
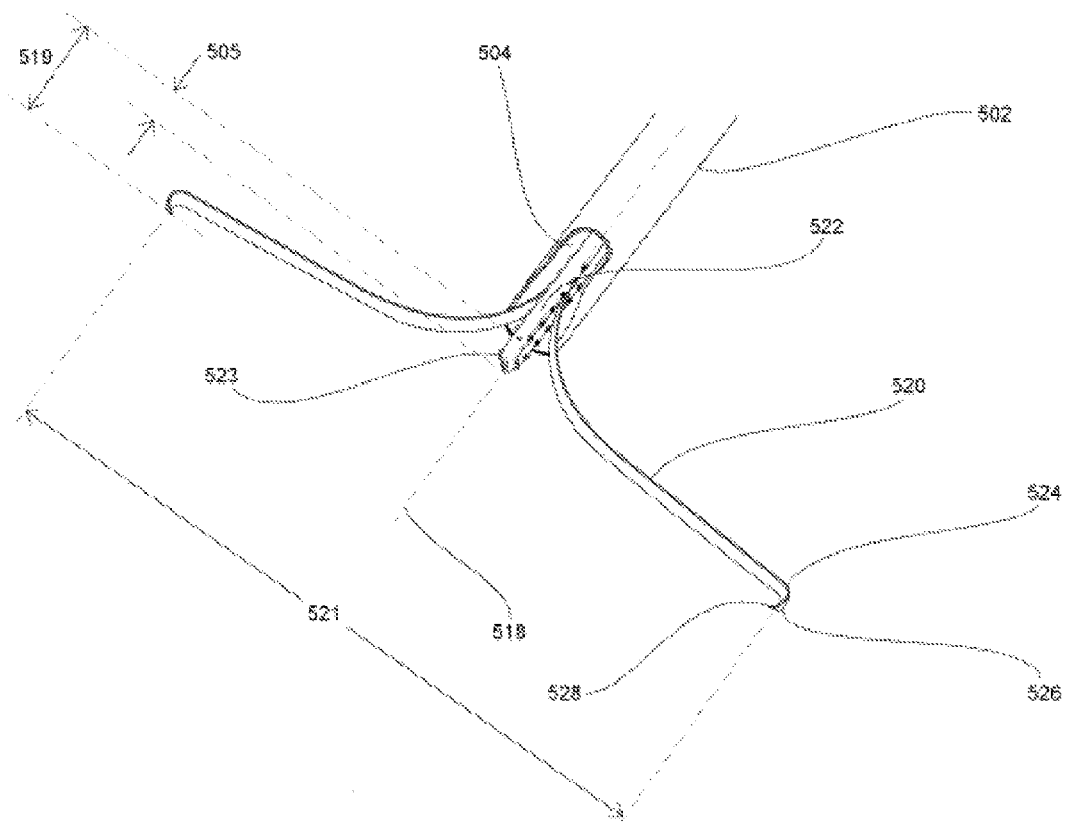

FIG. 5C shows an enlarged view of the distal end of tissue approximation device 500, with approximating tool assembly 508 being shown in the extended state, i.e. after being deployed by the operator. In this embodiment, extendible members 520 open, or extend, along a predefined path as they're released from the distal end of the shaft. An actuating mechanism such as plunger 514 is operatively connected to extendible members 520, such that when plunger 514 is axially displaced into handle assembly 506, extendible members 520 move distally along longitudinal axis 518 and thereby extend outward from working channel 504 beyond the end of elongate tubular member 502. After deployment to an expanded state, each of extendible members 520 is positioned with its distal ends 524 spaced apart from and positioned on opposite sides of longitudinal axis 518 from an opposing extendible member.

The degree of extension of the extendible members, and the spacing 521 between distal ends 524 of extendible members 520 may be governed by the degree of deployment out of shaft 502. In some embodiments, both the degree of extension of distal ends 524 from the shaft 504, indicated as longitudinal spacing 519, and the distance between extended distal ends 524 are selectably controllable by the operator to facilitate tissue engagement at desired locations, and to facilitate the creation of a tissue plication of the desired dimensions, thereby producing the desired gastric volume reduction.

Tissue approximating device 500 illustrated in FIGS. 5A-5F additionally comprises a pushing member 522 operatively connected to an actuator, such as slider 512, such that when slider 512 is translated away from its proximal (fully refracted) position, the distal end of pushing member 522 moves along longitudinal axis 518, thereby extending out of working channel 504 a distance 505 beyond the end of elongate tubular member 502. The extension of pushing member 522 facilitates invagination of a tissue fold and formation of a tissue plication as two or more tissue sites are approximated. Pushing member 522 may be operated independently of, or in coordination with, extendible members 520. In one embodiment, pushing member 522 is extended out of working channel 504 as the extendible members 520 are extended and the tissue engagement mechanisms are positioned to engage tissue.

Illustrative operation of a tissue approximation device 500 illustrated in FIGS. 5A-5F is described below. Following insertion of the shaft into the intra-abdominal space and positioning of the distal end of the shaft near a desired tissue approximation site, extendible members 520 are deployed from a collapsed state to an expanded state to prepare the device for subsequent tissue engagement steps. In one embodiment, extendible members 520 are expanded by an actuator that pushes the members out of, or releases them from the shaft, as follows. In this case, extendible members 520 are produced from a highly flexible and elastically deformable material (e.g. flexible polymers, flexible metals, shape change materials and combinations thereof may be used) and are made in a shape when in the expanded state having an outward (i.e. away from longitudinal axis 518) curvature. As the extendible members 520 are released from the working channel 504, they assume their expanded state, and the distal tissue engagement mechanisms are brought into contact with the tissue surface. Due to their flexible nature and outwardly curved shape, extendible members 520 flex elastically and continue to assume a progressively more extended condition as the operator continues releasing them from the shaft, causing distal arm portions 524 to slide outward along the tissue surface, becoming spaced apart, until the distal tissue engagement mechanisms are located in the desired positions for tissue engagement, as described below.

In another embodiment, extendible members 520 are designed to be released from the collapsed state to the expanded state in a self-actuating manner, automatically achieving the desired tissue engagement configuration when extended out of working channel 504 beyond the end of elongate tubular member 502. Such self-actuating motions can be achieved by various methods known in the art. For example, in one preferred embodiment of the present invention, extendible members 520 are produced from a highly elastic material (e.g. spring steel, hardened stainless steel, a shape change material such as a superelastic NiTi alloy, superelastic polymer, or the like) and are formed during manufacturing into the desired final deployed shape by mechanical and/or thermomechanical processing means known in the art. Extendible members 520 are then biased (i.e. mechanical potential energy is stored, similar to a pre-loaded spring) by elastically deforming and loading them into working channel 504 to thereby provide the device in its collapsed state. As extendible members 520 are then pushed out of working channel 504 during deployment, the stored energy is released and extendible members 520 automatically return to the pre-determined shape desired for subsequent tissue engagement when brought into contact with the tissue surface. It will be appreciated that different assemblies of extendible members having different dimensions, different curvatures, different elastic properties, and the like may be provided for use in a tissue approximating device of the present invention and an operator may select an appropriate extendible member assembly having the desired dimensions and extension properties and install the desired assembly in the working channel prior to an intervention.

In yet other embodiments, deployment of extendible members 520 from the collapsed state to the expanded state may be accomplished, by means of an actuating mechanism, by any combination of manual pushing to cause expansion and self-actuating expansion mechanisms. Factors that may be adjusted to optimize the above described reconfiguration and deployment motions include, for example, the cross sectional shape, curvatures, mechanical properties, length, etc. of extendible members 520. It should also be obvious to those skilled in the art that, within the scope of the present invention, other mechanical actuation mechanisms of providing the desired reconfiguration and deployment to adjust the extendible members from the collapsed state to the expanded state may also be used. Such actuating mechanisms may comprise, for example, springs, levers, cams, gears, linkages, and the like may be used.

Figure 5D:
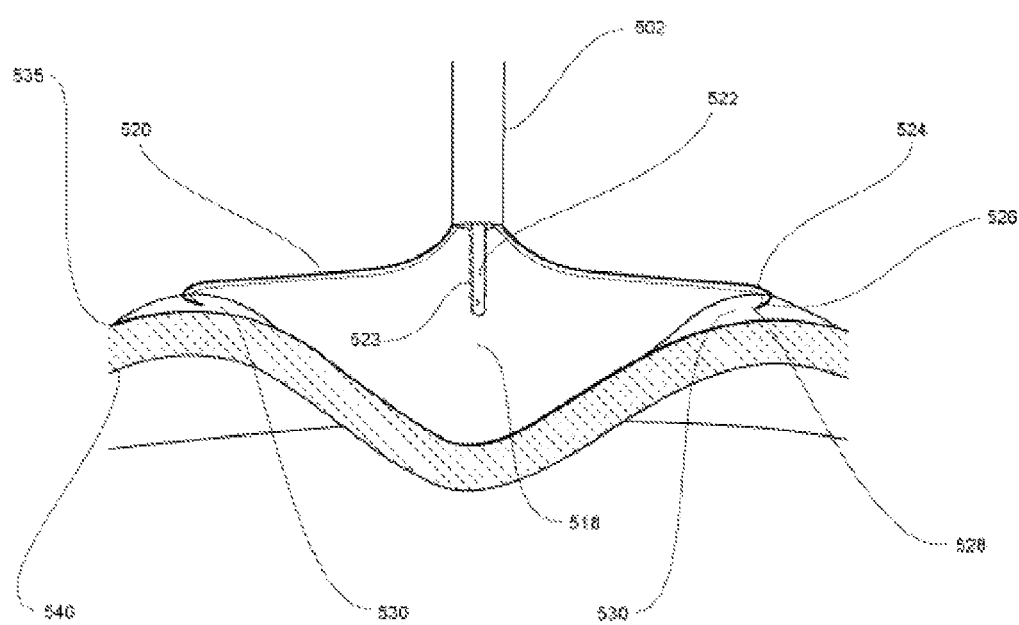

Distal ends 524 of extendible members 520 each incorporate one or more tissue engagement means configured to allow targeted tissue surface 535 to be selectively and controllably engaged by the device when actuated by the operator. Various tissue engagement mechanisms are known in the art may be employed to provide secure and robust tissue engagement having sufficient strength, for example, to allow the tissue to be subsequently pulled or otherwise manipulated without disengaging, slipping or tearing. Tissue engagement mechanisms that may be used include, for example, hooks, barbs, grippers, teeth, clamps, jaws, clips, t-tags, and the like. According to one embodiment of the present invention, as shown in FIG. 5C, tissue hooks 526 are located at the distal ends 524, and further comprise sharpened points 528 to promote tissue penetration. While extendible members 520 are in the expanded state, distal ends 524 and tissue hooks 526 are positioned such that sharpened points 528 curve slightly downward (distally) and inward (toward longitudinal axis 518). As a result, when pushed slightly downward onto the surface of the tissue, elastic deformation of extendible members 520 causes distal ends 524 to first move slightly outward. Then, when extendible members 520 are either lifted slightly (e.g. by the surgeon lifting device 500) or alternatively, when retraction of the extendible members is initiated by the operator (as described below), tissue hooks 526 move slightly downward and inward, thereby causing sharpened points 528 to pierce, penetrate and securely engage the tissue at tissue engagement locations 530, as shown in FIG. 5D. Preferably, distal ends 524, tissue hooks 526 and sharpened points 528 are designed such that secure tissue engagement is achieved by penetrating only the serosal tissue surface 535 (i.e. the serosal tissue layer), or a combination of the serosal and muscularis tissue layers, without penetrating the mucosal tissue surface 540.

While more complicated mechanical tissue engagement means may be employed in accordance with the present invention (e.g. hinged jaws, mechanical clamps, forceps, grippers, vacuum actuated mechanisms, and the like) there are several advantages to the embodiment described above, and similarly designed self-actuating embodiments. One advantage, for example, is that it is a simple, single component design having low production cost. Additionally, successful operation of this device is not particularly dependent upon operator technique (i.e. no sophisticated hand motions or unusual device manipulations are required), successful operation instead being more dependent upon device design factors that control, for example, the directions and magnitudes of the forces generated by extendible members 520 during the pushing and pulling motions involved in deployment and/or retraction of the device. Examples of design factors that may be optimized in the self-actuating design embodiments of the present invention include the shape, physical dimensions, geometrical angles, surface finish, and the like, of extendible members 520, distal ends 524, tissue hooks 526, and sharpened points 528, as well as their materials of manufacture and mechanical properties.

In one embodiment, extendible members 520 have a non-circular, generally flattened cross section to effectively increase the lateral (i.e. out of plane) stiffness when extendible members 520 are extended. Examples of suitable non-circular cross sectional shapes include square cross sections, rectangular cross sections, triangular cross sections, arcuate cross sections, hemispherical cross sections, oblong or flattened cross-sections, and combinations of the foregoing. The cross sectional shape, physical dimensions, mechanical properties, and so on, of extendible members 520 may be designed having variations along their length to provide improved deployment, tissue engagement or retraction characteristics.

Figure 5E:
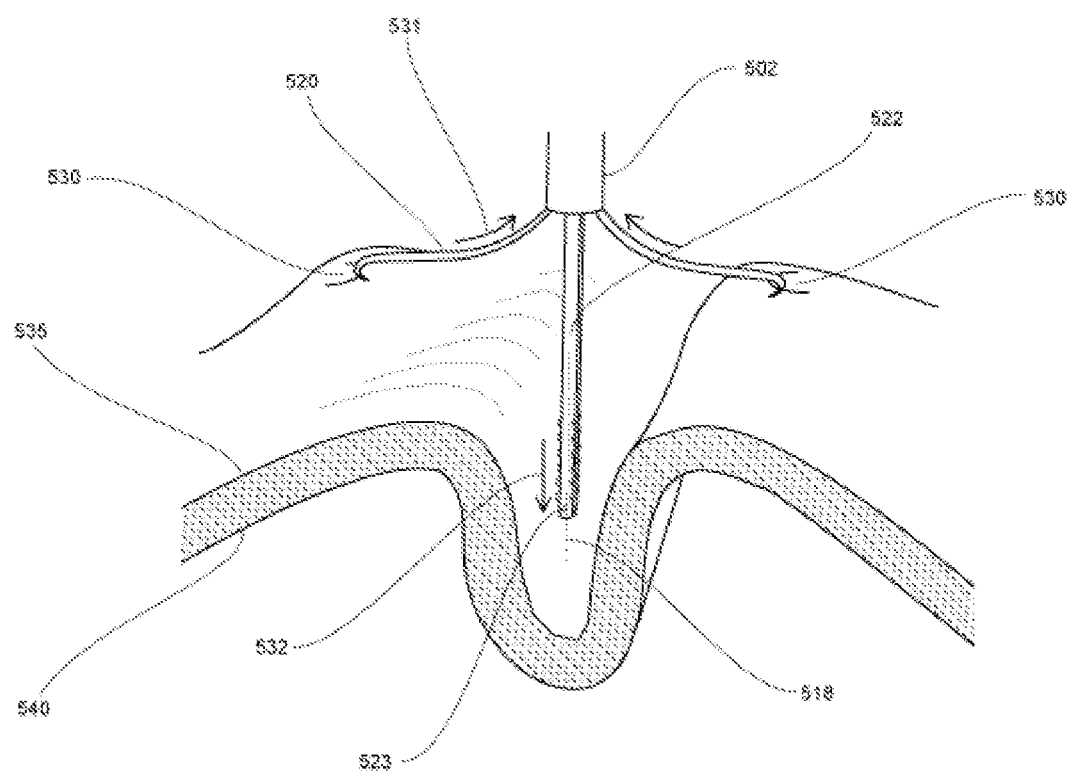

In another embodiment, extendible members 520 have a pre-determined shape when in the expanded state that includes at least two bends having radii of curvature in substantially opposing directions. Such a shape, as illustrated in FIGS. 5C-5E and explained above, may be utilized to initially give rise to a slight downward motion of distal ends 524, in addition to the inward motion that occurs during the retraction of extendible members 520 back into working channel 504, wherein the combined initial downward and inward motions of distal ends 524 effectively promotes tissue penetration and secure tissue engagement of sharpened points 528 on tissue hooks 526 upon actuated retraction of extendible members 520. The combined initial downward and inward motions of distal ends 524 that promote tissue penetration and secure tissue engagement may also be achieved using other designs obvious to those skilled in the art. This embodiment simplifies the operation, improves consistency, reduces procedural times and risk of complications, by minimizing reliance on individual operator technique and instead taking advantage of highly controlled and repeatable device motions.

After tissue has been securely engaged by approximating tool assembly 508, as described above, the operator actuates device 500 to initiate the tissue invagination and approximation step, wherein the desired tissue fold is formed by bringing serosal tissue surfaces between the engaged tissue sites in contact with each other, so that the mucosal tissue surface 540 forms a plication extending into the gastrointestinal lumen. FIG. 5E illustrates this process. In the example provided, the operator selectively activates device 500 remotely using trigger 510 provided within handle assembly 506, which is operatively connected to extendible members 520 in a manner such that, as trigger 510 is squeezed, extendible members 520 are thereby controllably retracted and pulled back into working channel 504, as indicated by retraction forces 531. The mechanisms used to operatively connect trigger 510 to extendible members 520 may include various mechanical elements known to those skilled in the art, such as gears, transmissions, levers, pivots, linkages, and the like, whether manual or automated, in order to provide the retraction forces at the working (distal) end of the device, while keeping the actuating mechanisms operated by the operator at a convenient level.

Figure 5F:
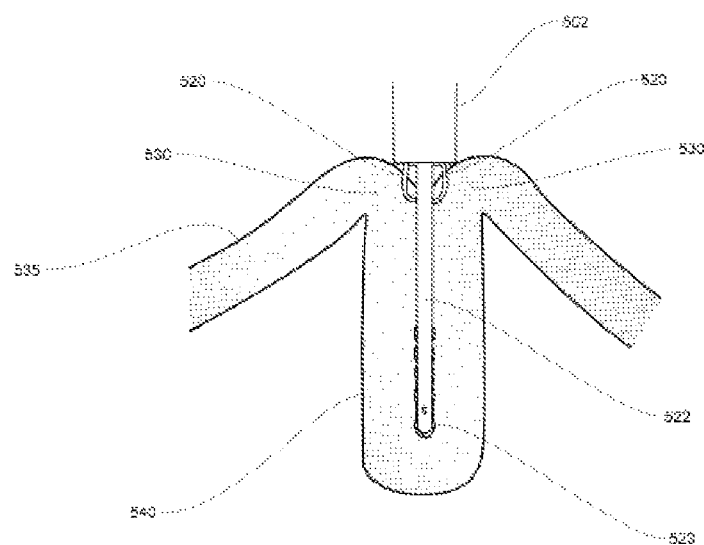

The retraction of extendible members 520 causes tissue engagement locations 530 to be gradually pulled inward toward longitudinal axis 518. In one device embodiment that incorporates a pushing member, the operator may selectively and independently actuate pushing member 522 from within handle assembly 506 (i.e. using slider 512) as the tissue engagement locations are drawn toward one another. The pushing member is extended distally along longitudinal axis 518 to contact and push against the tissue, e.g. with pushing force 532, at a location between tissue engagement points 530. This promotes tissue invagination in the desired manner while the engaged tissue is approximated, as shown in FIG. 5E. Once extendible members 520 have been fully retracted by complete actuation of trigger 510, the tissue engagement locations 530 have been brought into approximation near the distal end of elongate tubular member 502 to create tissue fold 540 as shown in FIG. 5F. In this illustration, pushing member 522 is shown remaining in the fully extended position.

The combination of extendible members and a pushing member in devices of the present invention, enabling the combined action of pulling tissue engagement points 530 toward one another via retraction of extendible members 520 while simultaneously having the user selectable option to push against the tissue between tissue engagement points 530 with pushing member 522 promotes creation of a uniform and consistent tissue fold, as shown in FIG. 5F. In preferred embodiments of the present invention therefore, operation of the device in the described manner effectively approximates opposing serosal tissue surfaces 535 inside the tissue fold, providing substantially intimate serosa-to-serosa contact, without forming wrinkles, bunches, gaps, or the like, and without penetrating the mucosal tissue surface 540.

In other embodiments of the present invention, additional user selectable controls may be optionally provided within handle assembly 506. For example, controls may be optionally provided to allow the surgeon to adjust the span 521 of extendible members 520 when in the expanded state, and the distal extension distance 505 and pushing force 532 of pushing member 522. Independent, operator controlled actuation mechanisms may be provided for each of the more than one extendible member 520, and the actuation mechanisms may control the speed and force that may be used to retract extendible members 520, as well as other operating parameters. It should also be recognized that the actuation means described above are exemplary, and that other actuation and control mechanisms that are known to those skilled in the art may be used and are considered within the scope of the present invention. For example, actuation may be accomplished manually by one or more various means known in the art (e.g. triggers, levers, buttons, knobs, or the like) or by one or more various powered means known in the art (e.g. AC or DC electric motors, compressed gas, vacuum, or the like), or by any combination of the foregoing.

As described previously, according to one embodiment of the present invention, it is desirable to selectively and therapeutically treat the serosal tissue layer to promote bonding or adhesion of the serosal layers that abut one another within the plication. This may be accomplished using device 500 in various ways. For example, in one embodiment illustrated in FIGS. 5C-5F, the distal tip and/or lateral surfaces of pushing member 522 may be used to mechanically disturb and disrupt the thin layer of mesothelial cells that form the outermost covering of the serosa. Since the layer of mesothelial cells covering the serosa is quite thin and fragile, it is easily disrupted, and pushing member 522 may be scraped, dragged or otherwise frictionally moved across the surface of the tissue to produce the desired disruption. To further aid in disrupting the serosal tissue surface and promote tissue adhesion, pushing member 522 may be modified, for example, by incorporating roughening features 523, illustrated as protuberances in FIGS. 5C-5F. As will be obvious to those skilled in the art, a wide variety of such roughening features and arrangements may be used to accomplish the desired serosal treatment, for example, ridges, bumps, bristles, teeth, scales, serrations, and the like may be used.

The optional serosal treatment described above may be carried out before the tissue fold is formed, after the tissue fold is formed but prior to the securing means is applied, after the tissue fold is formed and the securing means is applied, or any combination of the foregoing. For example, prior to actuating extendible members 520 to engage tissue, the distal end of pushing member 522 may be moved across substantially the identified area of serosal tissue to be included within the tissue fold in a sweeping or painting type of motion. Alternatively, the lateral surfaces of pushing member 522 contact and slide across the opposing serosal tissue surfaces of the tissue fold when pushing member 522 is retracted from within the tissue fold (as is evident in FIG. 5F), thereby disrupting at least a substantial portion of the serosal tissue surface during normal device operation. In this case, roughening features 523 present on the lateral surfaces of pushing member 522 may ensure more uniform and consistent serosal treatment, leading to a more effective and stronger serosa-to-serosa tissue bond.

In another serosal treatment embodiment, ports may be provided near the distal tip of shaft 502 and/or along pushing member 522 such that, when the shaft and/or pushing member lumen is connected to a supply of source material (e.g., a liquid reservoir located within or attached to the proximal handle assembly 506), the device provides controlled dispensing of a chemical or therapeutic agent (e.g. liquid, gas, solid powder, solid film, or combinations thereof) onto the tissue surface that promotes tissue bonding and adhesion. Alternatively, the distal tip of shaft 502 and/or pushing member 522 may optionally incorporate an energy deposition mechanism capable of delivering energy to the target tissue. Exemplary energy deposition mechanisms include, for example, components capable of RF cauterizing, electrocauterizing, ultrasonic vibration, and the like.

According to the present invention, once the tissue has been approximated and the desired tissue fold has been created as described above, fasteners are then applied to secure the plication. This is most conveniently accomplished while approximating tool assembly 508 is held in place by the operator to maintain the tissue in a stable, folded configuration. In one embodiment, a separate interventional instrument may be introduced through a separate trocar, and its distal tip may be positioned immediately adjacent approximating tool assembly 508. This instrument is then actuated to apply a fastener directly into and across the shoulders of the approximated tissue forming the tissue fold, thereby securing the plication. In this embodiment illustrated in FIG. 6A, a system 600 of the present invention comprises two separate handheld devices, each device capable of being actuated using controls located at their respective proximal handle assemblies. A first device 620 incorporates an approximating tool assembly 625 which may be substantially similar to approximating tool assembly 508, described above, at its distal end, and a second device 640 incorporates a fastening tool assembly 645 at its distal end, capable of applying a fastener to the tissue fold to secure the plication. A wide variety of a suitable fasteners are known to those skilled in the art and may be suitably be used as fasteners within the broad scope of the present invention. Exemplary fasteners comprise, for example, sutures, box-type staples, U-shaped or hemispherical fasteners, helical fasteners, clips, tacks, wall anchors, t-tags, and the like. A commercially available laparoscopic stapler, suturing device or tack applicator may be used to secure the tissue fold.

Figure 6A:
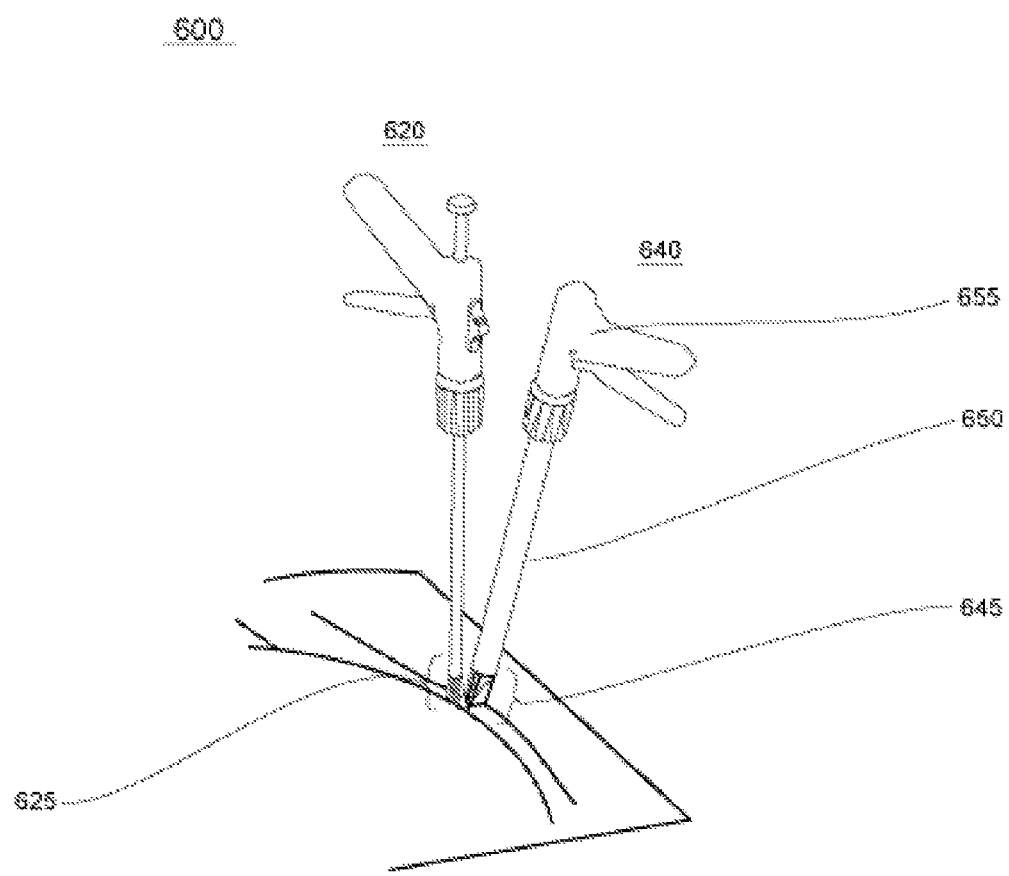

Accordingly, the laparoscopic interventional stapler shown in FIG. 6A comprises an elongate tubular shaft 650 having at its proximal end a handle assembly 655 containing user controls, actuation mechanisms, and so on, and having at its distal end a fastening tool assembly 645, which incorporates mechanisms known in the art for feeding, deploying, forming and applying to the target tissue a plurality of fasteners. These fasteners are most commonly made from stainless steel, titanium or NiTi, although other materials may also be used (e.g. other biocompatible alloys, polymers, bioabsorbable materials, and the like). Typically, a plurality of such staples would be provided within a disposable (i.e. single patient use) cartridge that is loaded at the distal end of the device, allowing multiple staples to be placed consecutively by the operator without removing the device from the patient.

Figure 6B:
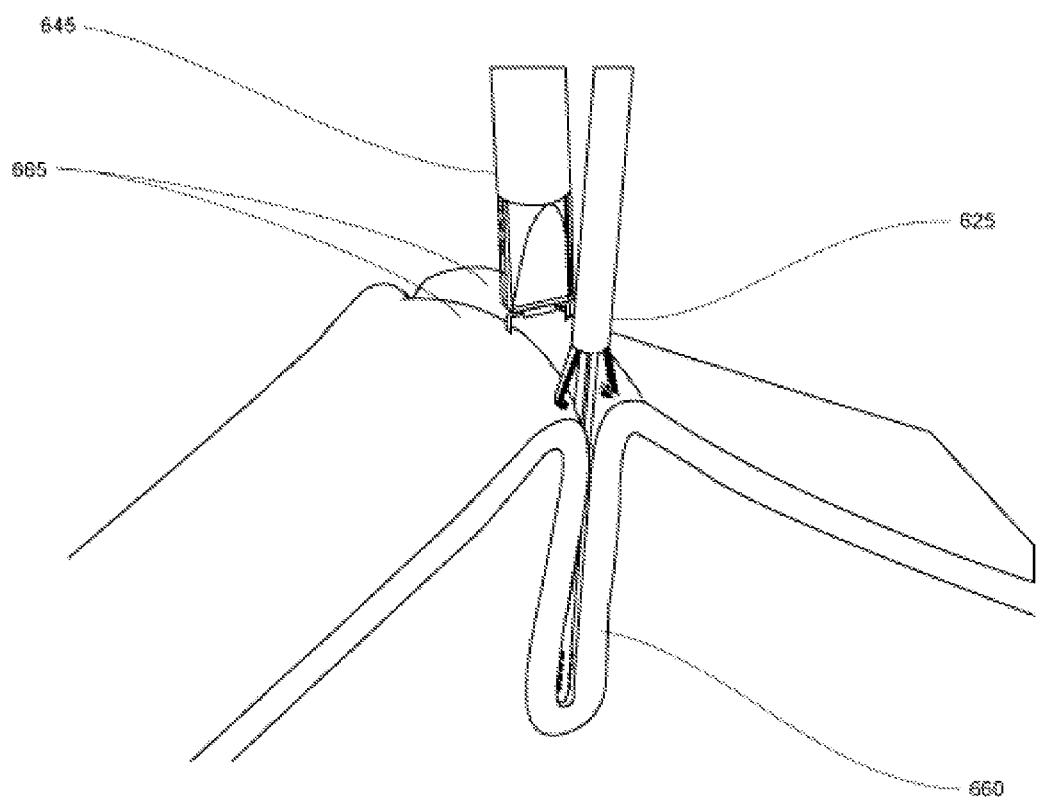
Figure 6C:
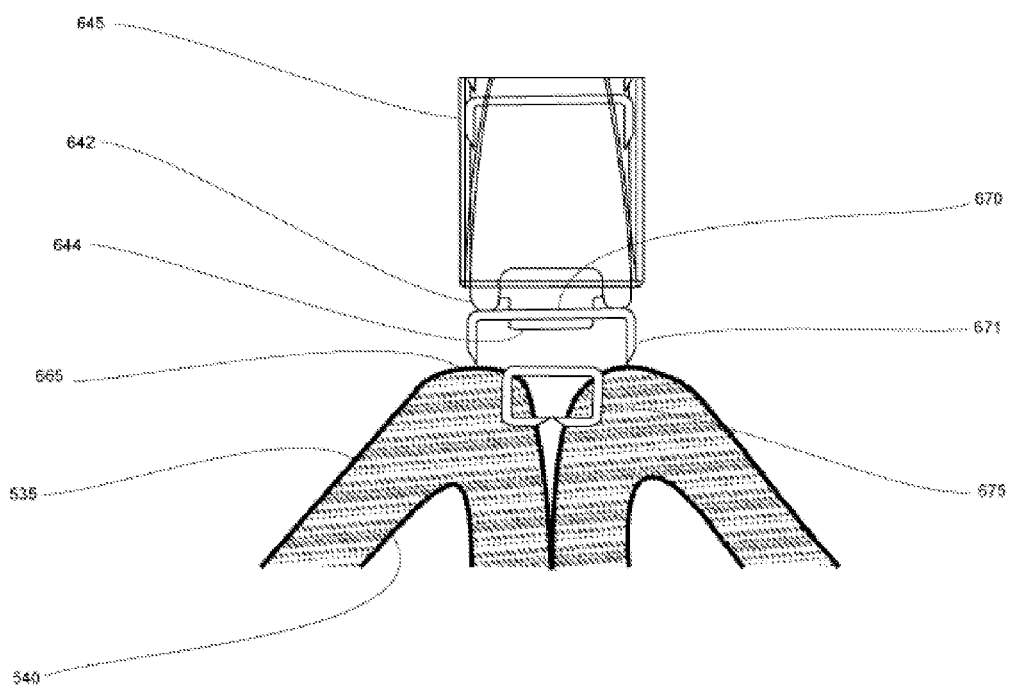
Figure 6D:
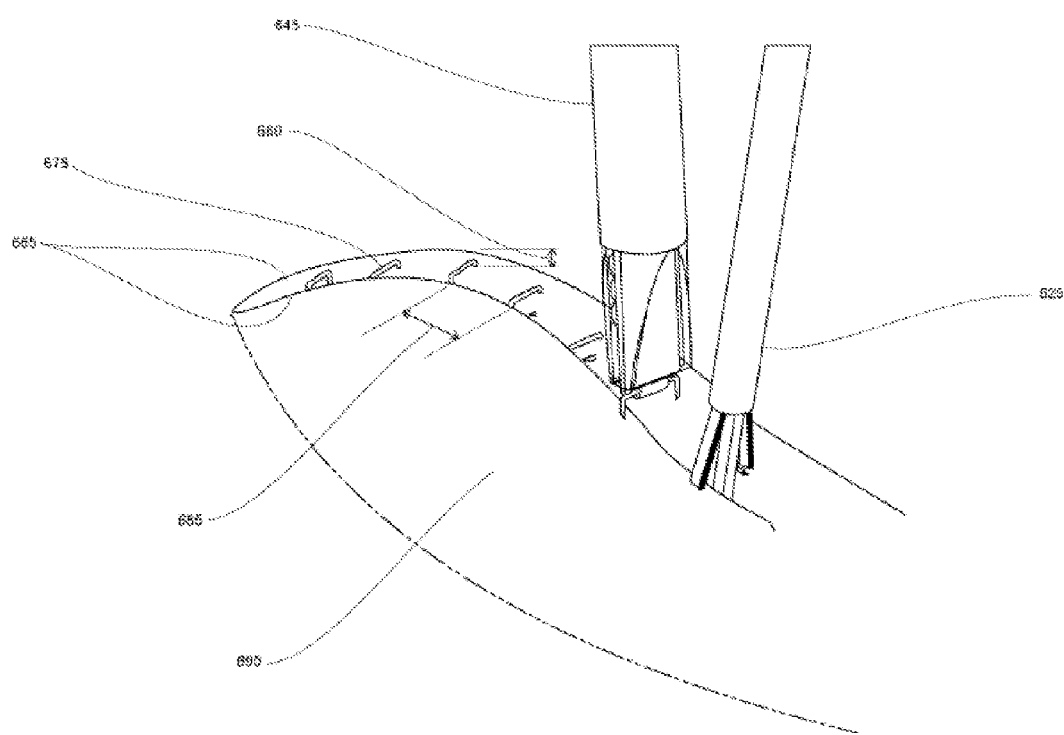

FIG. 6B shows a close up view of the distal ends of device 620 and device 640, indicating the preferred relative positioning of approximating tool assembly 625 and fastening tool assembly 645, respectively, according to one embodiment of the present invention. In this view, approximating tool assembly 625 has previously been deployed, the tissue has been engaged, and the extendible members have been retracted (these steps being carried out e.g. as described in FIG. 5), in order to create tissue fold 660. Shoulders 665 of tissue fold 660 are approximated near the distal tip of approximating tool assembly 625, and are held in position, ready for the tissue fastener to be applied by fastening tool assembly 645. The cross sectional view of FIG. 6C shows a close up of the distal tip of fastening tool assembly 645. In this example, a box-type staple in the pre-deployed state 670 is shown loaded within the within fastening tool assembly 645. Prior to applying the staple, fastening tool assembly 645 is positioned such that staple legs 671 of box-type staple in pre-deployed state 670 are positioned substantially perpendicular to, and in contact with, shoulders 665 of the tissue fold. When the surgeon fires the stapler using actuation means provided within the proximal handle assembly, extendible pistons 642 extend distally, deforming staple legs 671 around stationary anvil 644 and thereby reconfiguring the box-type staple into deployed state 675 as it is ejected from the device. As the staple is deployed, it penetrates the tissue and simultaneously pulls opposing tissue shoulders 665 toward one another, as shown. Note in this example that the box-type staple in deployed state 675 engages only the outermost layers of gastric tissue, i.e. serosal layer 535 and/or the muscularis tissue layers (not shown), and that there is no penetration through the gastric wall, which preserves the mucosal tissue layer 540 intact. FIG. 6D schematically illustrates a plication being secured using several consecutively repeated applications of the above described procedure. Approximating tool assembly 625 and fastening tool assembly 645 are shown, along with a multiplicity of individual box-type staples in the deployed state 675 that have been applied and which are arranged in a substantially continuous row extending along the length of tissue shoulders 665 to secure plication 690 projecting into the gastrointestinal space. The depth 680 below the surface and spacing 685 between the individual staple placements may be selectively controlled by the operator.

In another embodiment of the present invention, the tissue approximating and fastening functions described above requiring the use of two separately operable handheld interventional instruments are combined into a single multi-functional device having one or more integrated tools capable of invaginating and approximating tissue to create a tissue fold, as well as one or more integrated tools for applying fasteners to secure the plication. By combining these functions conveniently in a single handheld device, the overall procedure is simplified, and it can be performed without requiring extensive operator training. Furthermore, the need for one laparoscopic access port is eliminated, which provides a significant advantage.

Figure 7A:
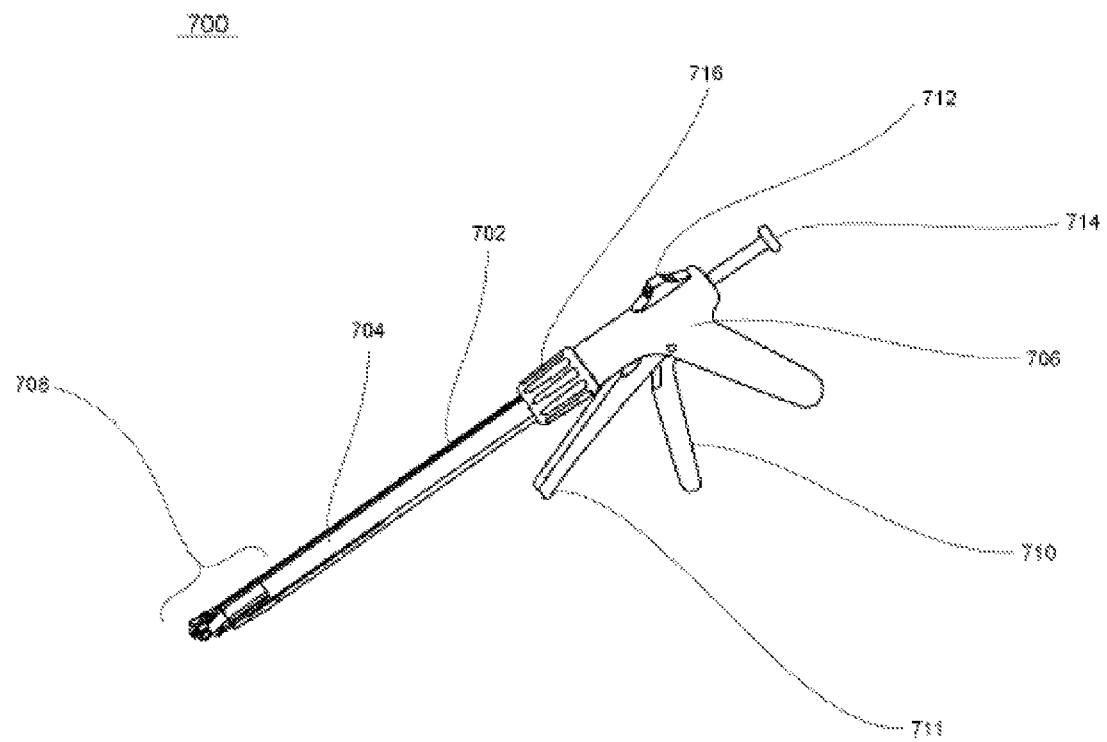

FIGS. 7A-7H illustrates such an integrated device and its operation, according to one embodiment of the present invention. Device 700 comprises an elongate tubular member 702 having internal working channel 704 and handle assembly 706 positioned at the proximal end. At the distal end of device 700 is multi-functional tool assembly 708, shown in the collapsed (i.e. pre-deployment or fully retracted) state in FIG. 7A. It is generally desirable that the outer diameter of elongate tubular member 702 be as small as possible, preferably 20 mm or less, more preferably 15 mm or less and, in some embodiments, 12 mm or less. The embodiment illustrated in FIG. 7A, illustrates actuating mechanisms used to operate the device, namely first trigger 710, second trigger 711, slider 712, and plunger 714 provided in connection with handle assembly 706. Also shown is rotating collar 716 that allows the orientation of handle assembly 706 to be independently adjusted by the user relative to the orientation of approximating tool assembly 708.

Figure 7B:
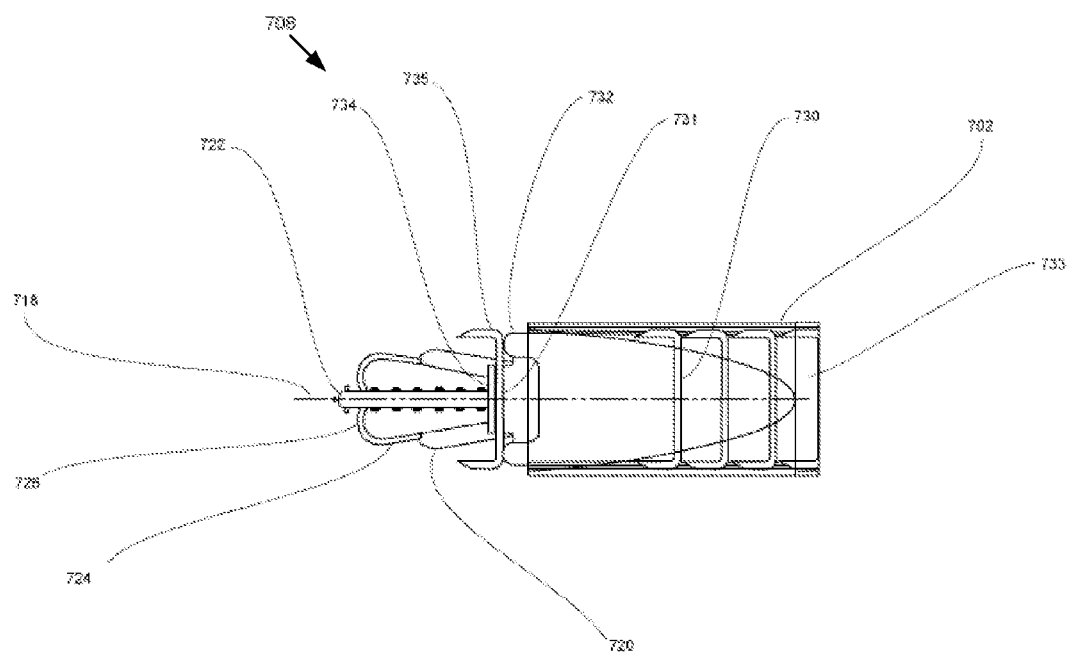

A close up cross sectional view of the distal end of device 700 is shown in FIG. 7B, illustrating details of multi-functional tool assembly 708 in the collapsed state. Multi-functional tool assembly 708 combines substantially similar structural and functional elements as previously illustrated in and described with reference to FIGS. 5 and 6. Accordingly, in this configuration, located along longitudinal axis 718 of working channel 704 are two (or more) extendible members 720, and (optional) pushing member 722, each being operatively connected to actuating mechanisms accessible to an operator at handle assembly 706. Each of the extendible members 720 is configured at its distal end with a distal tip 724, and each distal tip 724 incorporates one or more tissue engagement mechanisms whose working function is to controllably and selectively grasp, grab, grip, pierce, hold or otherwise engage tissue. In the example shown, distal tips 724 incorporate tissue hooks 726. Box-type staples in pre-deployed state 730 are loaded into working channel 704 and are configured (using, for example, guide channels and a spring loading mechanism) to slidably move toward the distal end of multi-functional tool assembly 708 and into the pre-fire position 731 as staples are sequentially ejected from the device. Pistons 732 are positioned at the distal end of shaft 733, and, along with stationary anvil 734, are used to deform staple legs 735 and thereby reconfigure and eject the staples when the device is actuated by the user, as described below.

Figure 7C:
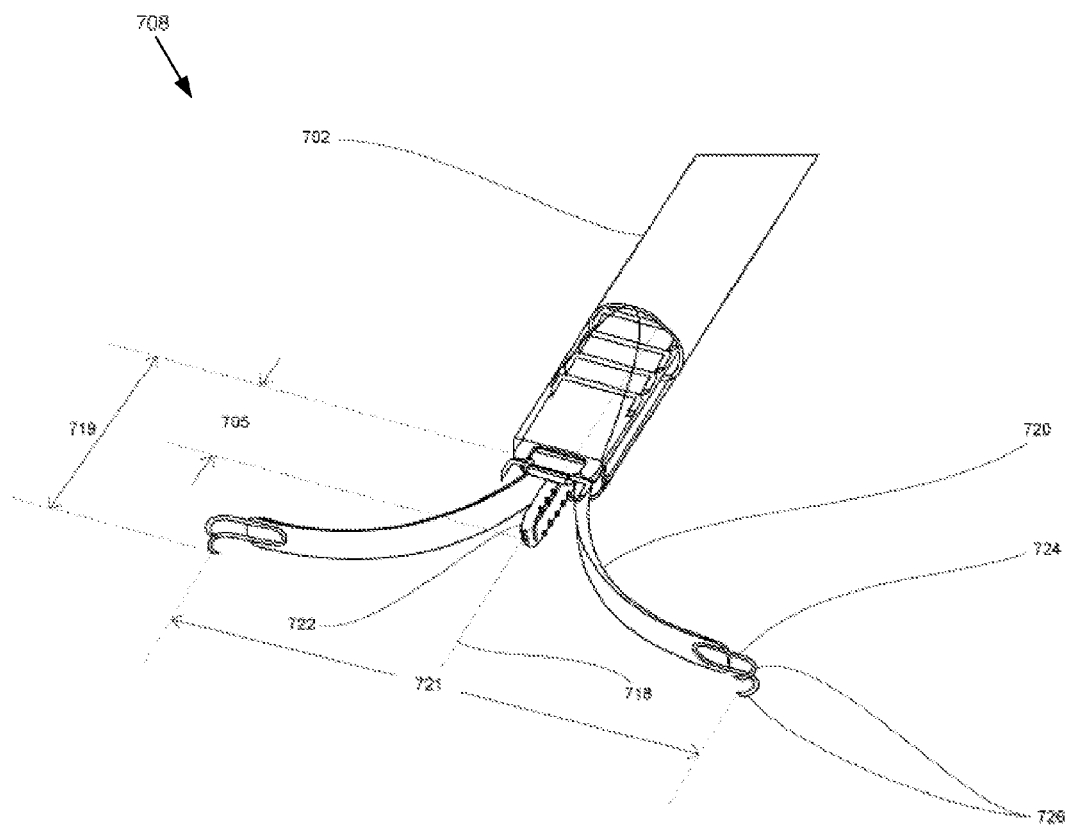
Figure 7D:
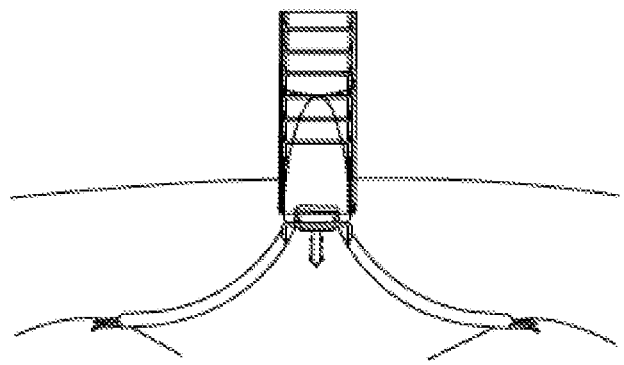
Figure 7E:
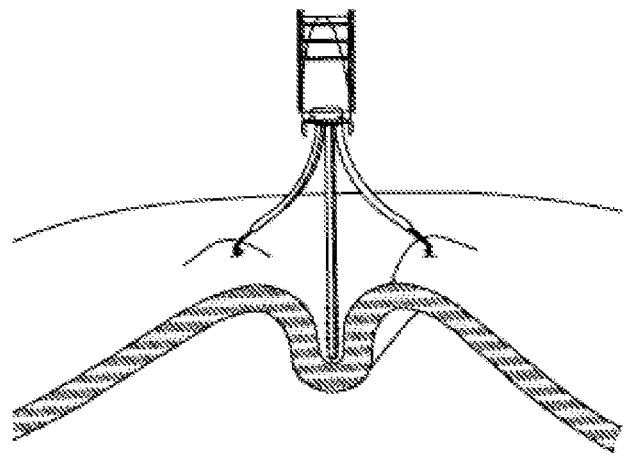
Figure 7F:
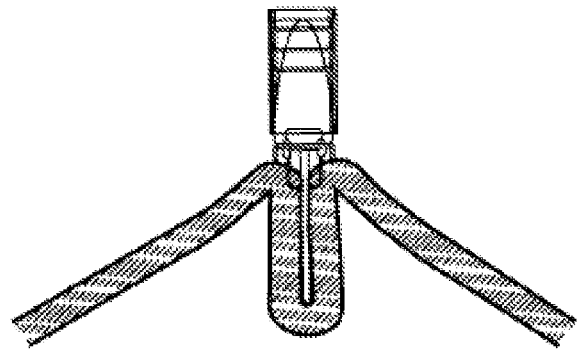

FIG. 7C illustrates a close up view of multi-functional tool assembly 708 having extendible members and tissue engagement mechanisms in the extended state, i.e. after being deployed by the operator. In the embodiment illustrated, plunger 714 is operatively connected to extendible members 720, such that when plunger 714 is pushed into handle assembly 706, extendible members 720 move distally along longitudinal axis 718 and thereby extend outwardly from working channel 704 and beyond the end of elongate tubular member 702. During deployment to the extended state, each of extendible members 720 is positioned such that distal tips 724 are spaced apart from one another and positioned on opposite sides of longitudinal axis 718. In the example shown, extendible members 720 have a flattened cross sectional configuration to increase lateral stiffness and prevent undesirable out-of-plane bending during deployment. Distal tips 724 of the extendible members 720 may comprise multiple tissue hooks 726, which facilitate secure tissue engagement and help to prevent undesired out-of-plane bending of extendible members 720 during deployment. Both the longitudinal positioning 719 and spacing 721 of arm tips 724 may be selectably controlled by the user to facilitate the desired positioning of tissue engagement members 726 and the subsequent size and position of the tissue plication formed by approximating the tissue.

Device 708 additionally incorporates pushing member 722, which is operatively connected to slider 712, such that when slider 712 is pushed from its proximal (fully retracted) position, the distal end of pushing member 720 moves along longitudinal axis 718, thereby extending out of working channel 704 a user selectable distance 705 beyond the end of elongate tubular member 702. The pushing member facilitates invagination and folding of the tissue between the engaged portions and may, additionally, function to disrupt the serosal tissue surface, or facilitate application of a tissue bonding promoter, as described above. Operation of the pushing member may be independent of, or coordinated with, extension and retraction of the extendible members and tissue engagement mechanisms.

Figure 7G:
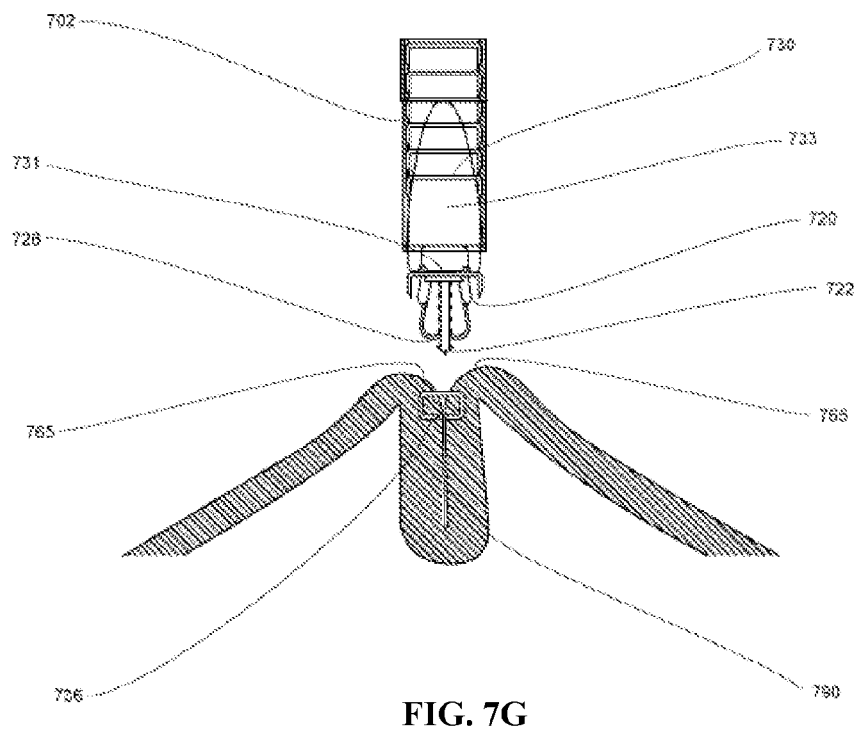

The steps of deploying device 700, engaging tissue, and invaginating and approximating tissue to create a tissue fold are substantially similar to what was previously described with reference to FIGS. 5D-5F. For the sake of clarity, these sequential steps are again illustrated in FIGS. 7D-7F with reference to operation of multi-functional tool assembly 708. After the tissue has been approximated and the fold has been created, device 700 is positioned in a suitable location for the subsequent step of applying one or more fasteners to secure the plication. Accordingly, similar to corresponding FIG. 6C, FIG. 7G illustrates the distal portion of device 700 after the device has been actuated from within handle assembly 706 using a second trigger 711, which is operatively connected to extendible shaft 733. The actuation, as described previously, forms and ejects a box-type staple, reconfiguring it by deformation from the pre-deployed state 730 to the deployed state 736, and securely implanting the staple within the tissue as described previously. This results in penetration and pulling together of the opposing tissue shoulders 765, which thereby secures the created tissue plication 790 projecting into the gastrointestinal space. Tissue hooks 726 may then be operatively disengaged from the tissue using a slight forward actuation of plunger 714 located within handle assembly 706, after which extendible members 720 may be completely retracted back into the shaft of the device by full reverse actuation of plunger 714. Pushing member 722 may also be completely retracted back into the device, using reverse actuation of slider 712. The serosal tissue layer may be treated to promote bonding during manipulation of the pushing member, as discussed previously. The next in line pre-loaded staple in the pre-deployed state 730 automatically (for example, via spring pressure) moves into the pre-fire position 731, and the device is therefore fully prepared and ready for repeating the entire sequence at the next tissue location selected by the operator, as shown in FIG. 7G.

Figure 7H:
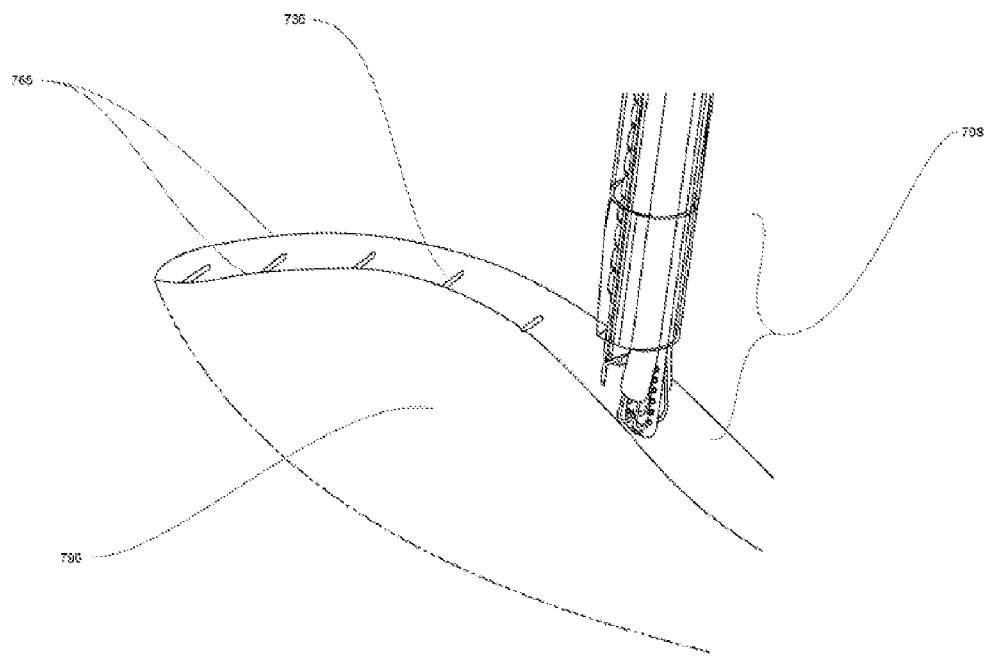

As illustrated in FIG. 7H (substantially similar to FIG. 6D), after repeating the procedural steps described above using multi-functional tool assembly 708, a plurality of staples in the deployed state 736 are implanted into and across tissue shoulders 765, securing plication 790 projecting into the gastrointestinal space. One or more such plications may be produced in this manner, each having the desired length, depth, etc., and each having a selectable number of implanted fasteners, fastener depth, fastener-to-fastener spacing, and so on, as previously described. Using the devices of the present invention in this manner, the operator is therefore able to achieve the desired gastric reduction laparoscopically and without ever needing to fully penetrate the gastric wall or otherwise compromise the internal mucosal tissue layer.

Figure 8A:
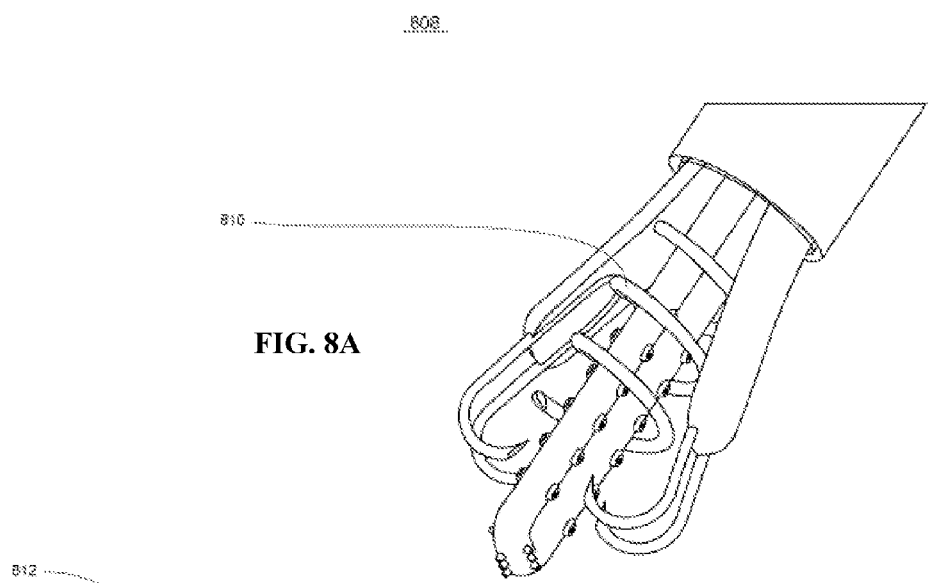
Figure 8B:
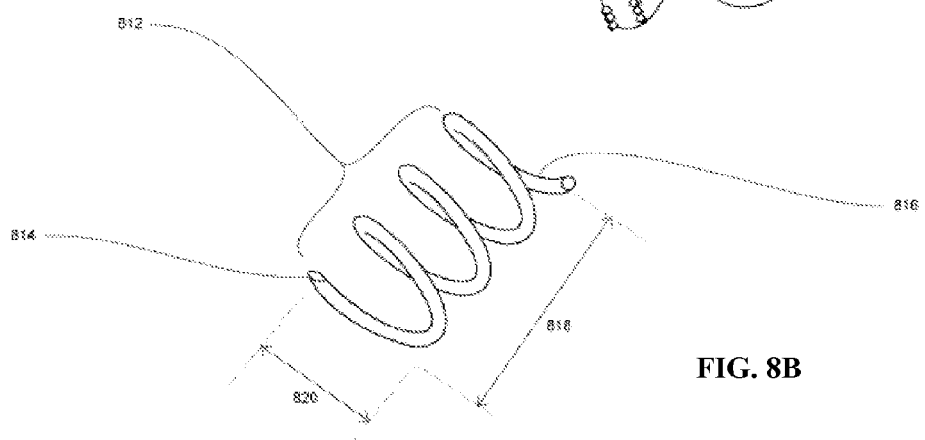
Figure 8C:
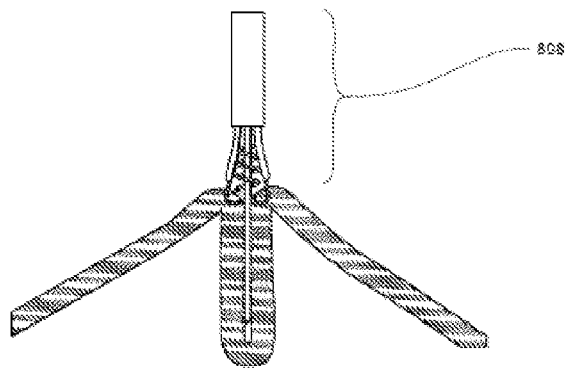

FIG. 8A illustrates a close up view of the distal end of a tissue approximation device according to another embodiment of the present invention. In this case, the device is a handheld instrument that is designed and operates similarly to device 700, and incorporates multi-functional tool assembly 808 at a distal end of the shaft. Multi-functional tool assembly 808 is similar to multi-functional tool assembly 708 described above, with the notable exception that the fasteners used in this embodiment are helical fasteners, shown as helical fastener 810 in FIG. 8A, as an alternative to the box-type staple described previously. Helical fastener 810 may be formed from wire having desirable characteristics (e.g. strength, stiffness, surface finish, anti-friction coatings, drug eluting coatings, and so on) and, as shown in FIG. 8B, includes body 812, sharpened leading tip 814 and proximal end 816. Fastener body 812 may have one or more screw- or coil-type turns, and is additionally characterized by length 818 and diameter 820, which may be optimized according to the desired depth and width of tissue penetration desired for various interventional procedures. Length 818 is preferably between 1 mm and 50 mm, more preferably between 2 mm and 40 mm and, in many embodiments, between 3 mm and 30 mm. Diameter 820 is preferably between 1 mm and 20 mm, more preferably between 2 mm and 15 mm and, in many embodiments, between 3 mm and 12 mm. Sharpened tip 814 is configured to aid in tissue penetration during deployment. Proximal end 816 is typically configured to allow operative engagement directly or indirectly to a rotating shaft located within the working channel of the elongate tubular member of device 800, such that when rotatingly actuated from within the handle assembly, the helical fastener rotates as it exits the distal end of the device, thereby penetrating the tissue. Helical fastener 810 may be fabricated from any suitable biocompatible material known in the art, for example stainless steel, Ti, NiTi, or the like may be used, as well as other materials such as polymers, ceramics, and combinations of the foregoing.

Figure 8D:
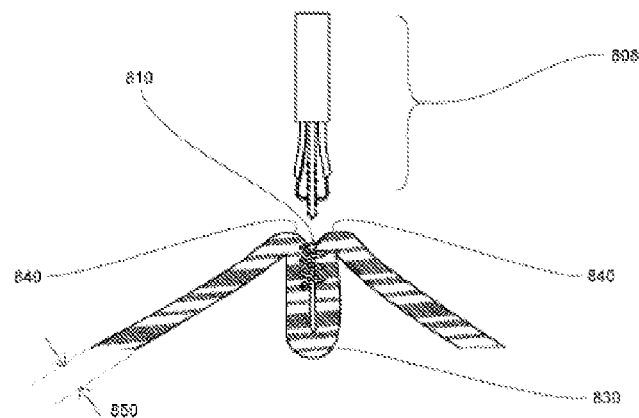
Figure 8E:
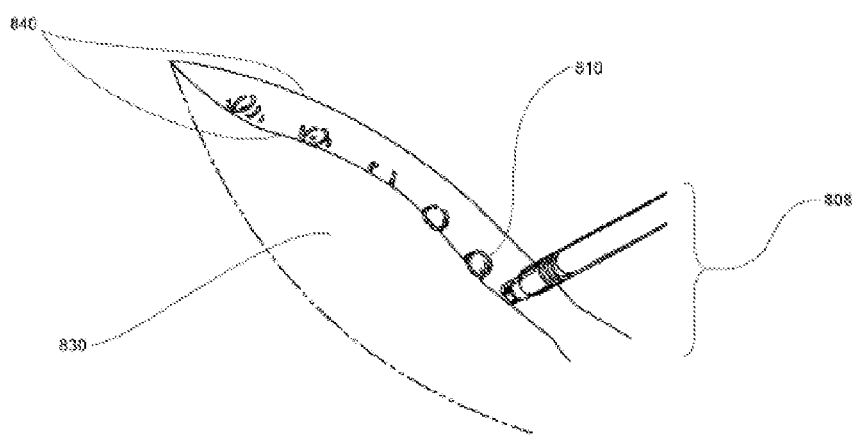

In using the device illustrated in FIGS. 8A-8E, the steps of deploying the device, engaging tissue and approximating tissue to create a tissue fold are substantially identical to what was described above regarding device 700, and illustrated in FIGS. 7A-7H. After the tissue fold has been created, multi-functional tool assembly 808 is in position and ready to apply the securing means, as illustrated on FIG. 8C. FIG. 8D shows multi-functional tool assembly 808 immediately after helical fastener 810 has been applied to the tissue fold to produce plication 830, illustrating the preferred placement location and orientation of helical fastener 810 between tissue shoulders 840. It is important that diameter 820 of helical fastener 810 be sized appropriately relative to the thickness of the tissue, and that proper orientation of the device is maintained (i.e. substantially perpendicular to the tissue surface and co-planar with the opposing tissue surfaces within the tissue fold), such that tissue on both sides of the tissue fold are repeatedly and consistently engaged as the helical fastener is deployed into the tissue during actuated rotation of device 800. Preferably, diameter 820 is approximately comparable to tissue thickness 850, more preferably it is between 0.5× and 1.5× tissue thickness 850, but in any case it is most preferably maintained at less than twice the tissue thickness 850 to avoid penetration completely through the stomach wall. Similar to FIG. 7H, FIG. 8E shows plication 830 projecting into the gastrointestinal space that was produced as a result of the repeated placement of device 800 and actuation of multi-functional tool assembly 808, wherein a plurality of helical fasteners 810 have been applied, as described previously.

There are advantages to using helical fasteners as securing means in methods and devices of the present invention. The mechanisms incorporated into devices for loading, feeding and deploying helical fasteners into the target tissue are simple to construct (e.g. few moving parts), compact, reliable, and easy to use. In general, helical fasteners require only rotation for deployment, and they don't necessarily involve reconfiguration from a pre-deployed state to a deployed state, as in the case of spring-type or deforming-type fasteners. Also, helical fasteners may be deployed such that the fastener repeatedly engages tissue at multiple points of contact over a relatively large surface area on the opposing tissue surfaces. This leads to effective load distribution and tends to reduce the maximum forces generated on both the tissue and fastener, resulting in less likelihood that either the tissue or the fasteners will fail. The use of helical fasteners may thus increase the mechanical robustness of the plication produced and improve the long-term prognosis for a successful interventional outcome.

Figure 9A:
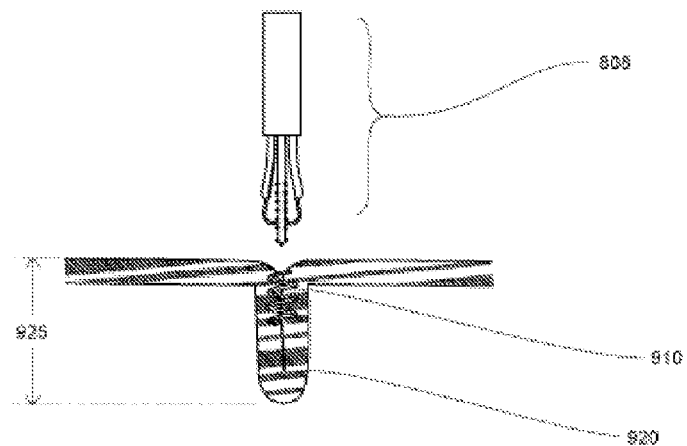
Figure 9B:
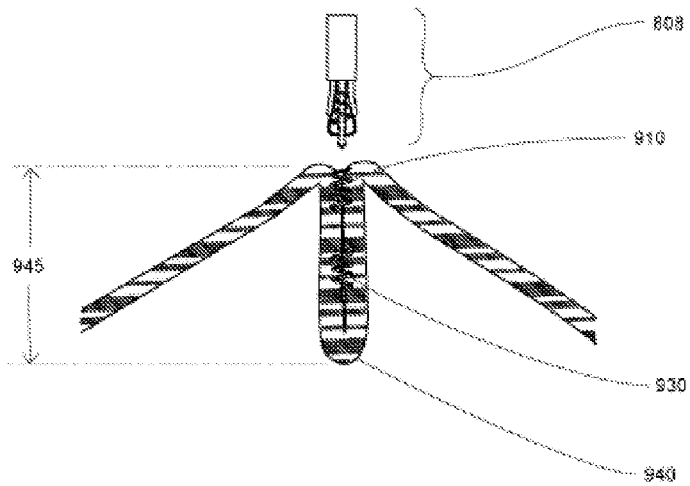

In certain situations, it may be desirable and advantageous to (optionally) provide additional reinforcement to the opposing tissue surfaces within the tissue fold and resulting plication. Such additional reinforcement not only results in stronger securement of the plication and greater load distribution, but it may also provide stabilization against undesirable or excessive tissue motions, more intimate serosa-to-serosa contact and bonding, and increased rigidity to the gastrointestinal lumen (which may reduce the amount of stretching that occurs during digestion. Additional reinforcement may be accomplished using the methods and devices of the present invention by applying additional fasteners at a location within the plication as it is being produced, as illustrated in FIGS. 9A and 9B. FIG. 9A illustrates that multi-functional tool assembly 808 has been used to place first helical fastener 910, creating first plication 920 having depth 925, using the procedures described previously. Next, rather than move to the next tissue location to repeat the procedure (e.g. as shown in FIG. 8D), multi-functional tool assembly 808 is instead maintained at substantially the same tissue location and tissue approximation is repeated a second time, creating a second tissue fold directly over top of the initial plication. As shown in FIG. 9B, a second helical fastener 930 is then applied, thereby producing extended plication 940 having depth 945 (greater than depth 925), and having first helical fastener 910 completely inside the plication, acting as an additional securing means interior to the plication. This procedure may be repeated as many times as desired by the operator, resulting in the successive placement of interior fasteners and extension of the depth of the plication. Beyond the stated benefits of the additional interior fasteners, a significant advantage of building up the plication depth in this manner is that the maximum designed working span of the device (e.g. spacing 721 of arm tips 724 in FIG. 7C) may be reduced, resulting in a more compact and reliably operating device.

Figures 10A, 10B:
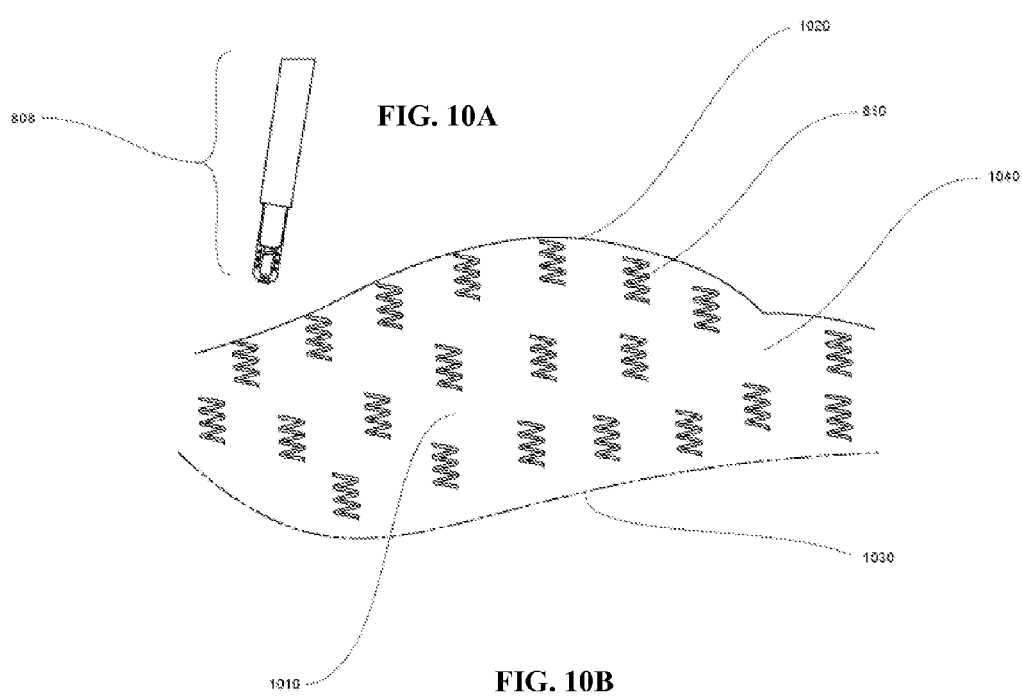
FIG. 10A illustrates a multifunctional tool for placing helical fasteners and FIG. 10B shows a plurality of helical fasteners applied to secure a tissue fold and thereby produce a plication.

As will be obvious to those skilled in the art, the concept of providing additional reinforcement to a plication through placement of interior securing means can be extended according to other embodiments of the present invention. For example, FIG. 10A illustrates a multifunctional tool for placing helical fasteners and FIG. 10B illustrates a cross sectional view of a laparoscopically produced plication 1010 projecting into the gastrointestinal space that was created entirely extragastrically using multi-functional tool assembly 808. A plurality of helical fasteners 810 have been placed at various locations along the length and depth of the plication, thereby ensuring substantially intimate serosa-to-serosa contact over substantially the entire tissue contact area inside the plication. In addition, using the devices of the present invention, the surgeon has complete flexibility while performing the procedure to accommodate natural patient-to-patient anatomical variations in organ shape, tissue thickness, texture, presence of defects, and the like.

Figure 11:
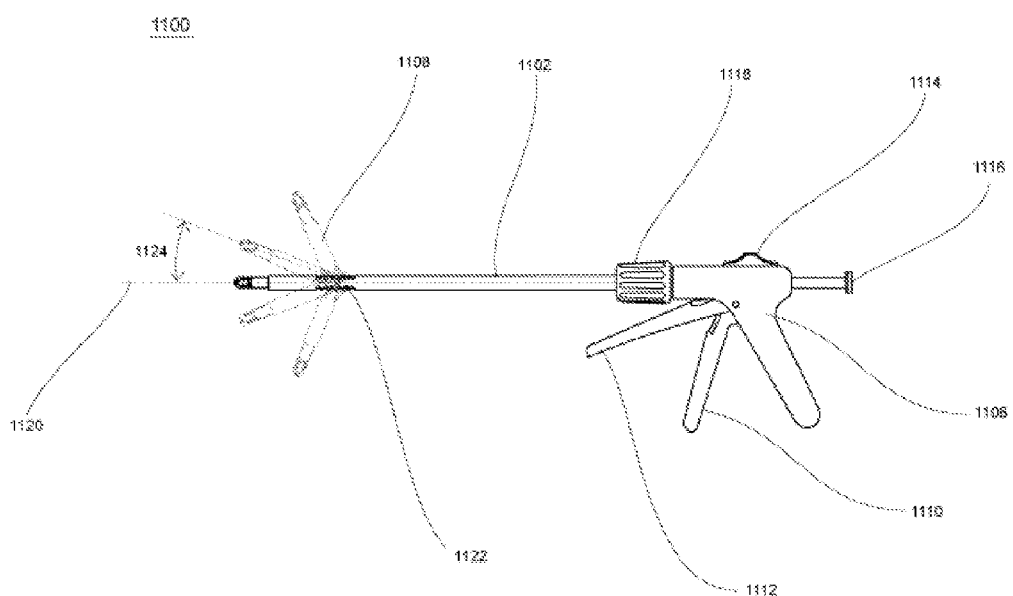
FIG. 11 shows another embodiment of the present invention involving articulation of the distal multi-functional tool assembly.

In another embodiment of the present invention illustrated in FIG. 11, device 1100 is substantially similar in many functional aspects to the previously described devices. Device 1100 has elongate tubular member 1102 having handle assembly 1106 at its proximal end and multi-functional tool assembly 1108 at its distal end. Handle assembly 1106 further comprises the various actuating means that are operatively connected to and useful for controlling the extendible elements of multi-functional tool assembly 1108, namely first trigger 1110 (used for actuating retraction of extendible members), second trigger 1112 (used for actuating deployment of fasteners), slider 1114 (used for actuating the pushing member), and plunger 1116 (used for actuating deployment of the extendible members). Rotating collar 1118 permits handle assembly 1106 to pivot around the longitudinal axis 1120 of elongate tubular member 1102 in a user selectable fashion.

In device 1100, at least one multi-functional tool assembly 1108 is operatively connected to the distal end of elongate tubular member 1102 at articulating joint 1122. Articulating joint 1122 incorporates a flexible coupling along elongate tubular member 1102, as well as flexible internal components that operatively connect the actuating mechanisms of handle assembly 1106 to multi-functional tool assembly 1108. This feature allows multi-functional tool assembly 1108 to be adjustably positioned by the user at tip angle 1124 relative to longitudinal axis 1120, as shown. Preferably, tip angle 1124 is adjustable between 0 and ±90 degrees and, in some embodiments, tip angle 1124 is adjustable between 0 and ±60 degrees, while in yet other embodiments, tip angle 1124 is adjustable between 0 and ±45 degrees. Any type of articulating joint design know to those skilled in the art may be used, e.g. hinge joints, ball joints, universal joints, bellows joints, and the like, may be used. In the example shown, articulating joint 1122 allows multi-functional tool assembly 1108 to pivot around a single axis perpendicular to longitudinal axis 1120, meaning that tip angle 1124 can be adjusted only within a fixed plane. For convenience, in FIG. 11 this is shown as the plane of handle assembly 1106; however, since handle assembly 1106 can rotate around longitudinal axis 1120 (by adjusting rotating collar 1118), the operator has complete relational control between handle position and distal tip orientation, which is extremely useful for rapid, safe and efficient device operation. While a single articulating joint and multifunctional tool assembly is illustrated in FIG. 11, it will be appreciated that multiple multifunctional tool assemblies and multiple articulating joints may be provided in interventional tools of the present invention.

It will be appreciated that while methods and devices of the present invention have been described specifically with reference to reducing gastric volume by invaginating and approximating a wall of the gastrointestinal tract to create at least one plication therein, there are many other applications for both methods and devices of the present invention. More generally, methods and devices of the present invention may be used to approximate and, optionally, fasten two tissue locations, and may be used in connection with a wide variety of tissue sites, and all of these applications are encompassed by the methods and devices of the present invention.

We claim:

1. A method for reducing gastric volume comprising: accessing an external surface of a wall of the gastrointestinal tract; positioning a distal end of a shaft of a laparoscopic instrument in proximity to the external surface of a wall of the gastrointestinal tract; sequentially engaging tissue at each of two or more tissue sites on the external surface of the wall of the gastrointestinal tract by positioning releasable tissue engagement mechanisms mounted on retrievable tethers at each of the two or more tissue sites; retrieving the tethers to draw engaged tissue at each of the two or more tissue sites toward one another, thereby approximating the tissue sites and forming a fold extending into an interior space of the gastrointestinal tract.

2. The method according to claim 1, additionally comprising fastening tissue in proximity to the approximated tissue sites by application of at least one fastener.

3. The method according to claim 2, wherein the fastening involves application of a staple.

4. The method according to claim 3, wherein the steps are repeated multiple times and the fold extending into the interior space of the gastrointestinal tract is fastened by a row of staples.

5. The method of claim 2, wherein the fastening involves application of a suture.

6. The method of claim 2, wherein the fastening involves application of a t-tag.

7. The method of claim 2, wherein the fastening involves penetrating fewer than all layers of the gastric wall.

8. The method of claim 2, additionally comprising repeating the steps recited any desired number of times and applying one or more internal tissue fasteners within the plication to facilitate securing the tissue across an interior of the fold.

9. The method according to claim 1, wherein fastening involves application of at east one fastener selected from the group consisting of: sutures, staples, screws, tacks, clips, hooks, clamps, t-tags, and helical fasteners.

10. The method according to claim 1, wherein the wall of the gastrointestinal tract is at least one of the anterior and posterior surfaces of the wall of the stomach.

11. The method according to claim 1, additionally comprising repeating the steps recited any desired number of times.

12. The method of claim 11, wherein the procedure progresses sequentially in one direction along a length of the fold.

13. The method of claim 11, additionally comprising fastening tissue in proximity to the approximated tissue sites by sequential placement of multiple tissue fasteners.

14. The method of claim 11, additionally comprising fastening tissue in proximity to the approximated tissue sites by placement of a single tissue fastener along a substantial length of the fold.

15. The method according to claim 1, wherein retrieving the tethers involves moving a cinching member through which the flexible tethers pass distally down the tethers, causing the engaged tissue locations to move toward each other, thereby approximating the tissue sites.

16. The method of claim 1, wherein the tissue within the fold is arranged to provide substantially intimate serosa to serosa contact within the tissue fold.

17. The method according to claim 1, additionally comprising treating the external surface of the gastrointestinal tract between the tissue sites forming the fold to promote bonding.

18. The method of claim 1, additionally comprising administering an agent that promotes bonding of the external surface of the gastrointestinal tract between the tissue sites forming the fold.

19. The method of claim 1, additionally comprising disrupting the external surface of the gastrointestinal tract between the tissue sites forming the fold.

20. The method of claim 1, additionally comprising fastening tissue in proximity to the approximated tissue sites by bonding of external surfaces of the gastrointestinal tract forming the fold.

21. The method of claim 1, additionally comprising removing at least a portion of the omentum to expose the external surface of the gastrointestinal tract.

22. The method of claim 1, wherein the external surface of the wall of the gastrointestinal tract is an external surface of the stomach.

23. The method of claim 1, wherein the steps are carried out using a single laparoscopic access port.

24. The method of claim 1, wherein the gastrointestinal tract is the stomach and the tissue fold decreases the functional volume of the stomach by at least 30%.

25. The method of claim 1, wherein the gastrointestinal tract is the stomach and the tissue fold decreases the functional volume of the stomach by at least 50%.

26. The method of claim 1, wherein the tissue fold is in the stomach and extends approximately longitudinally from near the fundus to near the pylorus.

27. The method of claim 1, additionally comprising visually identifying and indicating a target position, a length of a fold centerline and a location of bounding lines where tissue will be contacted prior to engaging the external surface.

28. The method of claim 1, additionally comprising establishing a pneumoperitoneum by insufflation prior to positioning the distal end of the shaft in proximity to the external surface of the wall of the gastrointestinal tract.

29. The method of claim 1, additionally comprising repeating the steps at additional tissue sites on the external surface of the wall of the gastrointestinal tract and forming a second fold extending into the interior space of the gastrointestinal tract.

30. The method of claim 29, wherein the two tissue folds run substantially parallel to one another.

* * * * *

UNITED STATES PATENT AND TRADEMARK OFFICE
CERTIFICATE OF CORRECTION

| | | |
|---|---|---|
| PATENT NO. | : 8,414,600 B2 | Page 1 of 1 |
| APPLICATION NO. | : 13/413640 | |
| DATED | : April 9, 2013 | |
| INVENTOR(S) | : Peter S. Harris et al. | |

It is certified that error appears in the above-identified patent and that said Letters Patent is hereby corrected as shown below:

In the Claims:

| Col. No. | Line(s) | Edits |
|---|---|---|
| 30 (Claim 9) | 30 | Replace "application of at east" with --application of at least-- |

Signed and Sealed this
Sixteenth Day of July, 2013

Teresa Stanek Rea
*Acting Director of the United States Patent and Trademark Office*